US008433525B2

United States Patent
Burba et al.

(10) Patent No.: US 8,433,525 B2
(45) Date of Patent: *Apr. 30, 2013

(54) METHOD AND APPARATUS FOR DETERMINING GAS FLUX

(75) Inventors: George Burba, Lincoln, NE (US);
Dayle McDermitt, Lincoln, NE (US);
Anatoly Komissarov, Lincoln, NE (US);
Tyler G. Anderson, Lincoln, NE (US);
Liukang Xu, Lincoln, NE (US);
Bradley A. Riensche, Firth, NE (US)

(73) Assignee: LI-COR, Inc., Lincoln, NE (US)

( * ) Notice: Subject to any disclaimer, the term of this patent is extended or adjusted under 35 U.S.C. 154(b) by 96 days.

This patent is subject to a terminal disclaimer.

(21) Appl. No.: 13/085,346

(22) Filed: Apr. 12, 2011

(65) Prior Publication Data

US 2011/0270534 A1   Nov. 3, 2011

Related U.S. Application Data

(63) Continuation-in-part of application No. 12/553,954, filed on Sep. 3, 2009, now Pat. No. 7,953,558, which is a continuation of application No. PCT/US2009/055936, filed on Sep. 3, 2009.

(60) Provisional application No. 61/323,283, filed on Apr. 12, 2010.

(51) Int. Cl.
G01N 31/00 (2006.01)

(52) U.S. Cl.
USPC .......... 702/23; 702/24; 702/50; 702/137; 73/1.06; 73/23.28

(58) Field of Classification Search .......... 702/23–24, 702/137
See application file for complete search history.

(56) References Cited

U.S. PATENT DOCUMENTS

| 4,288,062 A | 9/1981 | Gupta et al. |
| 5,670,999 A | 9/1997 | Takeuchi et al. |

(Continued)

FOREIGN PATENT DOCUMENTS

| JP | 8-273939 A | 10/1996 |
| JP | 11-307705 A | 11/1999 |

(Continued)

OTHER PUBLICATIONS

Burba, G., at al., Correcting Apparent Off-Season CO2 Uptake Due to Surface Heating of an Open Path Gas Analyzer: Progress Report of an Ongoing Study, American Meteorological Society, 27th Conference on Agricultural and Forest Meteorology (2006).

(Continued)

*Primary Examiner* — Jonathan C Teixeira Moffat
*Assistant Examiner* — Mischita Henson
(74) *Attorney, Agent, or Firm* — Leydig, Voit & Mayer, LLP; Gerald T. Gray

(57) ABSTRACT

A system and method to obtain correct gas density and flux measurements using (i) gas analyzer (open-path, or closed-path gas analyzers with short intake tube, or any combination of the two); (ii) fast temperature or sensible heat flux measurement device (such as, fine-wire thermocouple, sonic anemometer, or any other device providing fast accurate gas temperature measurements); (iii) fast air water content or latent heat flux measurement device (such as, hygrometer, NDIR analyzer, any other device providing fast accurate gas water content measurements); (iv) vertical wind or sampling device (such as sonic anemometer, scintillometer, or fast solenoid valve, etc.) and (v) algorithms in accordance with the present invention to compute the corrected gas flux, compensated for T-P effects. In case when water factor in T-P effects is negligible, the fast air water content or latent heat flux measurement device (item iii in last paragraph) can be excluded.

7 Claims, 5 Drawing Sheets

U.S. PATENT DOCUMENTS

| | | | |
|---|---|---|---|
| 5,838,008 | A | 11/1998 | Esler et al. |
| 6,121,617 | A | 9/2000 | Hirayama et al. |
| 6,317,212 | B1 | 11/2001 | Eckles |
| 6,369,387 | B1 | 4/2002 | Eckles |
| 7,365,352 | B2 | 4/2008 | Muta et al. |
| 2001/0045521 | A1 | 11/2001 | Prozzo et al. |
| 2001/0048079 | A1 | 12/2001 | Brunamoti et al. |
| 2006/0192097 | A1 | 8/2006 | Anttalainen |
| 2010/0110437 | A1 | 5/2010 | Furtaw et al. |
| 2010/0110438 | A1 | 5/2010 | Furtaw |

FOREIGN PATENT DOCUMENTS

| | | |
|---|---|---|
| JP | 2008-116263 A | 5/2008 |
| KR | 10-2006-0050193 A | 5/2006 |

OTHER PUBLICATIONS

Burba at al., "Introduction to the Eddy Covariance Method"[Presentation], Copyright 2007-2009 LI-COR, Inc, 141 pages total.; retrieved from the Internet: <http://www.licor.com/env/PDF/EddyCovariance_readonly.pdf>.

Burba et al., "Combining the Strengths of Open-Path and Closed-Path Designs into a Single CO2/H2O Gas Analyzer," American Geophysical Union Fall Meeting, San Francisco, California, Dec. 14-18, 2009.

Burba et al., "Eddy Covariance Fluxes of Carbon Dioxide and Water Measured With New Compact Gas Analyzer," 2nd Integrated Land Ecosystem-Atmosphere Processes Study Science Conference, Melbourne, Australia, Aug. 24-28, 2009.

Burba et al., "Eddy Covariance Measurements of CO2 and H2O Fluxes With New Compact Gas Analyzer," 10th International Congress of Ecology, Brisbane, Australia, Aug. 16-21, 2009.

Burba et al., "Measurements of CO2 and H2O Fluxes with New Enclosed Design and with Modified Open-path Design of Fast Gas Analyzers," European Geosciences Union General Assembly, Vienna, Austria, May 2-7, 2010.

Burba et al., "Measurements of Evapotranspiration and Carbon Dioxide Exchange Using New Compact Closed-Path Gas Analyzer and Eddy Covariance Technique," The 2009 International Annual Meetings of the ASA, CSSA, and SSSA. Pittsburgh, Pennsylvania, Nov. 1-5, 2009.

Burba et al., "New Compact Gas Analyzer for Eddy Covariance Measurements of Carbon Dioxide and Water Vapor Fluxes," 15th WMO/IAEA Meeting of Experts on Carbon Dioxide, Other Greenhouse Gases, and Related Tracer Measurement Techniques. Max-Planck-Institute for Biogeochemistry, Jena, Germany, Sepember 7-10, 2009.

Burba et al, "New CO2/H2O Gas Analyzer Combines the Advantages of Open-Path and Closed-Path Solutions," AsiaFlux-2009, Integrating Cross-scale Ecosystem Knowledge: Bridges and Barriers. Hokkaido University, Sapporo, Japan, Oct. 27-29, 2009.

Burba et al., Poster presentation "Small Closed-Path CO2-H2O Gas Analyzer for Eddy Covariance Measurements.," The 8th International Carbon Dioxide Conference. Max-Planck-Institute for Biogeochemistry, Jena, Germany. Sep. 13-19, 2009.

Burba et al., "New $CO_2$ and $H_2 0$ Gas Analyzer Design Combines Open-Path and Closed-Path Advantages," 2009 AmeriFlux Principal Investigator Workshop, DOE, Washington DC, Sep. 21-23, 2009.

Burba et al, "New CO2/H2O Gas Analyzer for Eddy Covariance Flux Measurements," 94th Ecological Society of America Annual Meeting, Albuquerque, New Mexico, Aug. 2-7, 2009.

Burba et al., Novel Design of an Enclosed $CO_2/H_2 0$ Gas Analyze for Eddy Covariance Flux Measurements, *Tellus*. p. 1-6, Jun. 10, Aug. 1-6, 2010.

Burba et al., "Two New Low-Power and Light-Weight Solutions for Fast Measurements of $CO_2$ and $H_2 0$ Ecosystem Exchange," 95th Annual Meeting of Ecological Society of America, Pittsburgh, Pennsylvania, 2010.

Clement. R., et al., "Improved Trace Gas Flux Estimation Through iRGA Sampling Optimization", *Agricultural and Forest Meteorology*, vol. 149, Dec. 6, 2008.

Grelle A., et al., "Fine-Wire Thermometer to Correct CO2 Fluxes by Open-Path Analyzers for Artificial Density Fluctuations", *Agricultural and Forest Meteorology*, vol. 147, Jun. 2007.

Lubken et al., "The Effect of Water Vapour Broadening on Methane Eddy Correlation Flux Measurements," Journal of Atmospheric Chemistry, Jul. 1991: 13(1):91-108.

Neftel, Albrecht et al., "N2O exchange over managed grassland: Application of a quantum cascade laser spectrometer for micrometeorological flux measurements," *Agricultural and Forest Meteorology*, (2010) 150:775-785.

Notice of Acceptance of Jun. 2, 2010 for Australian Application No. 2009292601.

PCT Search Report and Written Opinion of Jun. 30, 2009 for application PCT/US2008/082671.

PCT Search Report and Written Opinion of Nov. 2, 2009 for application PCT/US2009/055936.

PCT Search Report and Written Opinion of Dec. 28, 2011 for application PCT/US2011/032180.

Reba, M., et al., "An Assessment of Corrections for Eddy Covariance Measures Turbulent Fluxes Over Snow in Mountain Environments", *Water Resources Research*, vol. 45, Aug. 18, 2009.

"Field intercomparison of two optical analyzers for $CH_4$ eddy covariance flux rneasurements," *Atmos. Meas. Tech. Discus.*, (2010) 3:2961-2993, Tuzson, B. et al.

Webb, E., et al., Correction of Flux Measurements for Density Effects Due to Heat and Water Vapour Transfer, *Quart. J. R. Met. Soc.*, vol. 106, p. 85-100, 1980.

McDermitt, D.K. et al. "Effects of Temperature, Pressure and Water Vapor on Gas Phase Infrared Absorption by $CO_2$," Poster presentation, Dec. 1993; LI-COR, Inc. Publication, Lincoln, NE 68504, USA (Dec. 2008) (5 pages).

METHOD AND APPARATUS FOR DETERMINING GAS FLUX

CROSS-REFERENCES TO RELATED APPLICATIONS

This application claims the benefit of U.S. Provisional Application Ser. No. 61/323,283, filed Apr. 12, 2010, the disclosure of which is incorporated herein by reference in its entirety. The present invention is also a continuation-in-part of U.S. application Ser. No. 12/553,954, filed Sep. 3, 2009, which is incorporated herein by reference in its entirety.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND

Embodiments of the present invention relate generally to gas analysis and more particularly to the measurement of gas density to determine gas flux.

When gas density measurements are performed by scanning a single rotational line or a few-discrete lines of analyte with a single-mode tunable laser source, the measured signal is temperature and pressure dependent due to a combination of Boltzmann population distribution of rotational levels, Doppler broadening, and temperature-dependent pressure broadening of an individual line. These pressure and temperature effects could also be affected by the presence of water and other gases in the sampled air. The combination of all of these effects will be further referred to as T-P effects. In addition, if a constant mixing ratio gas is used at relatively constant pressure, measured gas density itself changes with temperature and water content due to thermal expansion and water dilution of the gas per the Ideal Gas Law.

When the temperature or water content of gas changes, T-P effects may lead to a large change in absorption, significantly affecting the gas density measurement. In general, the T-P effects are specific and different for each absorption line of each gas.

With slow measurements of gas density, taking seconds and longer, the T-P effects can be calibrated out because mean temperature and water content of gas in the sampling volume can be easily measured. With fast measurements of gas density, e.g., several or more times per second, it is difficult to correct for T-P effects on-the-fly because it would require accurate and precise measurements of gas temperature and water content integrated over the entire sampling cell volume, and recorded at the same exact moment when the absorption is measured.

Existing gas analyzers, especially for trace gases such as methane, nitrous oxide, isotopes of carbon dioxide and water, etc., are closed-path sensors requiring long intake tubes and powerful pumps to allow sample gas flow of 30-100 lpm (liters per minute) and more. The fast temperature changes are attenuated in these long intake tubes so slow temperature measurements can be used, but power consumption of such sensors systems goes up to 1000 Watts and more, making them difficult to use in remote locations where most of the natural gas exchange processes for these gases occurs.

BRIEF SUMMARY

In accordance with embodiments of the present invention, methods and apparatus allow for correcting gas flux for the T-P effects without a need for accurate and precise fast measurements of gas temperature and water content integrated over the entire sampling cell volume, and recorded at the same exact moment when laser absorption is measured.

In accordance with embodiments of the present invention, the methods allow for correcting gas flux for the T-P effects using conventional fast measurements of air temperature and gas water content located away from the gas sampling path, not integrated over gas sampling cell volume, and without a need to record temperature and gas water content at the same precise moment with laser absorption measurement. In addition, the proposed method allows using long term statistics (10 minutes-4 hours) to obtain reliable correction for T-P effects over the same integration interval as the flux measurements (usually 10 minutes-4 hours).

Embodiments of the present invention significantly simplify the instrumental requirements for fast gas flux measurement devices, because instead of making it mandatory to design an instrument with fully attenuated (or very well measured) fast gas temperature, pressure and water content in the entire cell, disclosed embodiments use temperature and gas water content records from external conventional sensors (such as, fine-wire thermocouple, sonic anemometer, or any other device providing fast accurate air temperature measurements, and any fast $H_2O$ instrument) positioned near the sampling path of the gas analyzer. The term "near" refers here to a distance ranging from 0 meters (i.e., within the sampling path) to several meters.

As a result, there is no need to design a gas analyzer with fully attenuated, eliminated, or very well measured fast gas temperature, pressure and water contend in the cell. The method allows designing relatively simple devices (open-path, or closed-path gas analyzers with short intake tube, for example 1 m long, or any combination of the two) with power demand 50-100 times below the present gas analyzers, yet with similar accuracy of gas flux measurements.

The embodiments works by accurately relating T-P effects caused by a fast change in temperature to the thermal expansion effect (as per Ideal Gas Law) caused by the same fast change in temperature, and by accurately relating T-P effects caused by a fast change in gas water content to the water dilution effect (as per Ideal Gas Law) caused by the same fast change in gas water content. Thus, well-quantified processes of the thermal expansion and water dilution can be used as a means for the correction of temperature expansion, water dilution, and T-P effects.

Embodiments according to the present invention comprise: (i) gas analyzer (open-path, or closed-path gas analyzers with short intake tube, for example 1 m long, or any combination of the two); (ii) fast temperature or sensible heat flux measurement device (such as, fine-wire thermocouple, sonic anemometer, or any other device providing fast accurate gas temperature measurements); (iii) fast air water content or latent heat flux measurement device (such as, hygrometer, NDIR analyzer, any other device providing fast accurate gas water content measurements); (iv) vertical wind or sampling device (such as sonic anemometer, scintillometer, or fast solenoid valve, etc.) and (v) algorithms to compute the corrected gas flux, compensated for T-P effects.

In the case where the water factor in T-P effects is negligible, fast air water content or latent heat flux measurement device may be omitted.

The capabilities of gas analysis according to the present invention are extremely important and useful in areas of research such as gas exchange studies, climate studies, and atmospheric experimental research because it is possible, using commercially available lasers, to design low-power gas analyzers for Eddy Covariance, Eddy Accumulation, airborne and marine methods and for other "fast" methods of measuring gas exchange, requiring accurate and precise gas density measurements several or more times a second. With the ability to correct for T-P effects due to high frequency temperature and air water content fluctuations, open-path sensors and closed-path sensors with short wide intake tubes can be provided to the scientific and gas monitoring communities, reducing power consumption of the scientific and monitoring systems from 1000 Watts to 10-20 Watts. Such sensors can be placed in remote locations of interest, powered by solar panels, or can be used as portable hand-held sensors for gas density measurements.

In accordance with one embodiment, a gas analysis data handling device is provided that typically includes a processor, a communication interface to receive data from one or more measuring devices, and a memory store for storing data received by the communication interface. The processor is typically configured to receive a plurality data, the plurality of data including a plurality of gas density measurement data for a target gas, a plurality of wind speed measurement data indicative of speed of movement of the target gas, a plurality of water vapor density measurement data indicative of water content in the target gas, a plurality of temperature measurement data, and a barometric pressure. The processor is also typically configured to determine a raw flux of the target gas based on the gas density data for the target gas and the wind speed measurement data, to determine a water dilution effect based on the water vapor density measurement data, to determine a thermal expansion value based on the temperature measurement data, and to determine an equivalent pressure based on the barometric pressure, the temperature measurement data, the water vapor density data, and a water vapor broadening coefficient. The processor is also typically configured to compute the gas flux of the target gas based on the raw flux, the water dilution effect, and the thermal expansion value, wherein at least one of the raw flux, the water dilution effect, or the thermal expansion value is adjusted by a multiplication factor determined based on an instrument response function of the instrument used to obtain the gas density measurement data, the response function relating actual gas density and measured gas density of the target gas as a function of temperature and equivalent pressure or similar parameter.

In accordance with another embodiments, a gas analyzer system is provided that typically includes a gas analyzer having an optical path and operable to produce a plurality of gas density measurements when a target gas flows across the optical path, a pressure sensor configured to measure barometric pressure, a wind speed detector disposed in proximity to the gas analyzer, and a temperature sensor disposed in proximity to the gas analyzer and clear of the optical path of the gas analyzer. The system also typically includes a controller configured to receive a plurality of gas density measurement data obtained by the gas analyzer, to receive a plurality of wind speed measurement data obtained by the wind speed detector, to receive a plurality of temperature measurement data obtained by the temperature sensor, to receive a plurality of water vapor density measurement data indicative of water content in the target gas, and to receive a barometric pressure, e.g., an average barometric pressure. The controller is also typically configured to determine a raw flux term of the target gas based on the gas density measurement data and the wind speed measurement data, to determine a thermal expansion term based on the temperature measurement data, and to determine an equivalent pressure based on the barometric pressure, the temperature measurement data, the water vapor density data, and a water vapor broadening coefficient. The controller is also typically configured to compute the gas flux of the target gas based on the raw flux term and the thermal expansion term, wherein at least one term being adjusted by a multiplication factor determined based on an instrument response function corresponding to the instrument used to obtain the gas density measurement data, the instrument response function relating actual gas density and measured gas density of the target gas as a function of temperature and equivalent pressure or similar parameter.

It should be appreciated that the measured pressure does not have to be average or barometric. The gas pressure could be mean (average) or instantaneous and can be recorded with a barometer or with any pressure sensing device other than a barometer.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

DETAILED DESCRIPTION

Figure 1:
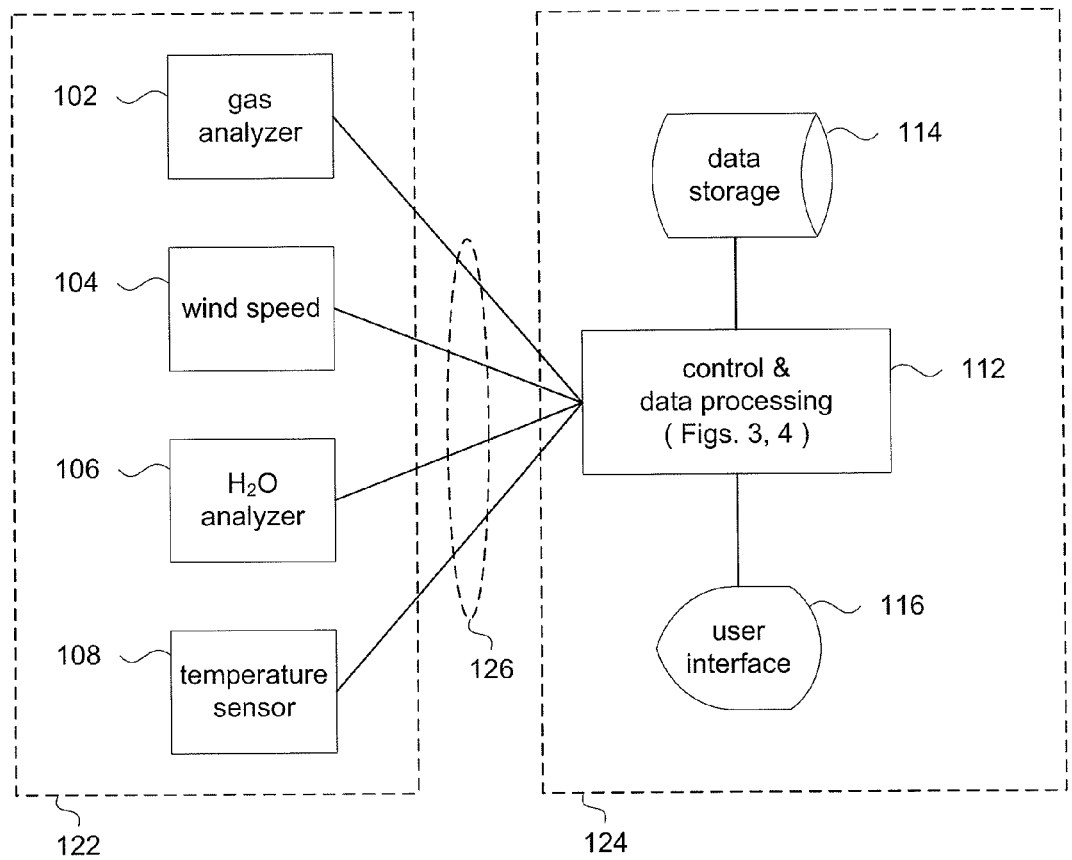
FIG. 1 illustrates a typical embodiment of a gas analysis system in accordance with the present invention.

Embodiments of the present invention relate generally to gas analysis and more particularly to the measurement of gas density to determine gas flux.

When gas density measurements are performed by scanning a single rotational line or a few discrete lines of analyte with a single-mode tunable laser source, the measured signal is temperature and pressure dependent due to the combined effects of Boltzmann population distribution of rotational levels and Doppler broadening and temperature-dependent pressure broadening of individual lines. These pressure and temperature effects can also be affected by the presence of water and other gases in the sampled air. The combination of all of these effects are referred to herein as T-P (temperature-pressure) effects. In addition, if a constant mixing ratio gas is used at a relatively constant pressure, then the measured gas density itself changes with temperature and water content due to thermal expansion and water dilution of the gas per the Ideal Gas Law.

When the temperature or water content of the gas changes, the T-P effects may lead to a large change in absorption, significantly affecting the gas density measurement. In general, the T-P effects are specific and different for each absorption line of each gas.

For slow measurements of gas density (e.g., measurements taken on the order of seconds and longer per measurement), the T-P effects can be easily calibrated out because the mean temperature and water content of the gas in the sampling volume can be easily measured. For the case of fast measurements of gas density (.e.g., several measurements taken per second), it is difficult to correct for T-P effects on-the-fly, because it would require accurate and precise measurements of gas temperature and water content integrated over the entire sampling volume. Moreover, the gas temperature and water content measurements would have to be recorded at the same moment when laser absorption due to gas density is measured.

Existing gas analyzers, especially for trace gases such as methane, nitrous oxide, isotopes of carbon dioxide and water, etc., are closed-path sensors requiring long intake tubes and powerful pumps to allow sample gas flow of 30-100 lpm (liters per minute) and more. The fast temperature changes are attenuated in these long intake tubes so slow temperature measurements can be used, but power consumption of such sensors systems goes up to 1000 Watts and more, making them difficult to use in remote locations where most of the natural gas exchange processes for these gases occurs.

Techniques of the present invention provide means to obtain correct gas density and flux measurements using (i) a gas analyzer (open-path, or closed-path gas analyzers with short intake tube, for example 1 m long, or any combination of the two); (ii) a fast temperature or sensible heat flux measurement device (such as, fine-wire thermocouple, sonic anemometer, or any other device providing fast accurate gas temperature measurements); (iii) a fast air water content or latent heat flux measurement device (such as, hygrometer, NDIR analyzer, any other device providing fast accurate gas water content measurements); (iv) a vertical wind or sampling device (such as sonic anemometer, scintillometer, or fast solenoid valve, etc.) and (v) algorithms in accordance with the present invention to compute a corrected gas flux that compensated for T-P effects. In a situation when the water factor in T-P effects is negligible, the fast air water content or latent heat flux measurement device (item iii above) can be excluded.

Teachings of the present invention are adaptable for any open-path or closed-path (with short intake tube, for example, 1 m long) gas analyzer that provide fast response measurements of gas density (several times per second). Embodiments of the present invention include the use of a temperature or sensible heat flux measurement device (such as a fine-wire thermocouple, sonic anemometer, scintillometer, etc.) providing fast accurate gas temperature or sensible heat flux measurements. In addition, when the water factor in T-P effects is not negligible, fast air water content or latent heat flux measurement device (described previously) or an estimate of mean latent heat flux is also factored in.

For the specific case of Eddy Covariance measurements of gas flux, a gas analyzer per the present invention can use fast measurements of vertical wind speed, and is readily adapted to use any wind speed measurements device (such as, sonic anemometer, etc.) that provides fast accurate measurements of vertical wind speed.

Generally, embodiments of the present invention comprise the following:
1. Calibrate gas analyzer versus temperature or use HITRAN (High resolution TRANsmission Molecular Absorption Database), and establish a T-P response surface describing T-P effects.
2. Install a fast temperature or sensible heat flux measurement device near the gas analyzer. Record fast temperature or sensible heat flux alongside the fast gas density.
   a. In case the water factor in T-P effects is not negligible, install a fast air water content or latent heat flux measurement device. Record fast air water content or latent heat flux alongside the fast gas density.
   b. For the case of Eddy Covariance gas flux measurements, install the anemometer device near gas analyzer, and record vertical wind speed alongside fast gas density.
3. Compute, measure, or estimate sensible heat flux by any conventionally known method. In case when water factor in T-P effects is not negligible, compute, measure, or estimate latent heat.
4. For the case of Eddy Covariance gas flux measurements, combine and align recorded time series of vertical wind speed and gas density measurements on a longer-term basis (minutes to hours), and compute raw uncorrected gas flux.
5. Compute gas flux corrected for T-P effects on spectral absorption. Frequency of data collection and averaging period (minutes to hours) are determined by the specific approach and purpose of the gas measurements.

A gas analyzer in accordance with the present invention provides gas flux that is corrected for T-P effects without the need for making measurements of fast gas temperature or air water content integrated over the gas sampling volume. This enables the use of low-power open-path gas analyzers as well as the use of reduced-power closed-path analyzers with short intake tubes. It is believed that no such analyzers relying on a single line, or narrow absorption range, are currently available.

First, a discussion will be given of algorithms and procedures according to the present invention used to obtain gas flux measurements that are corrected for the temperature and pressure conditions that existed during the collection of the measurement data. The discussion will then turn to illustrative embodiments of gas analysis in accordance with the present invention.

The discussion that follows explains the derivation of an algorithm for Eddy Covariance gas flux. In particular, the Webb-Pearman-Leuning (WPL) density term will be examined and modified in accordance with the present invention to account for T-P effects.

Derivation of Algorithm for Eddy Covariance Gas Flux Measurements

A. General Form of Propagation of T-P Effects of a Single-Line or Narrow Range Laser Measurement into Eddy Covariance Flux Measurements Let us define $\chi$ (chi) as the ratio of actual to measured gas densities as affected by T-P effects only, namely $\chi = \mathcal{F}(T, P, \text{etc.})$, excluding temperature-related gas expansion and water-related gas dilution effects. The function $\chi$ is also referred to variously as the instrument measurement response, instrument response, response function, measurement response function, and so on. In the most general form, $\chi$ could also include the effects of pressure broadening by water vapor and other possible air constituents, other spectroscopic effects and instrument-specific and method-specific response functions. $\chi$ could be written then in general form as follows:

$$\rho_c = \rho_{cm} \chi \quad (1)$$

where $\rho_{cm}$ is measured gas density that is not corrected for T-P effects, and $\rho_c$ is gas density that is corrected for T-P effects. Using Reynolds decomposition, each term can be written into following:

$$\rho_c = \rho_c' + \overline{\rho_c} \quad (2)$$

$$\rho_{cm} = \rho_{cm}' + \overline{\rho_{cm}} \quad (3)$$

$$\chi = \chi' + \overline{\chi} \quad (4)$$

where mean (average) quantities are indicated by the over-bar notation, the deviation of instantaneous quantity (i.e., the measured quantity) from the mean is indicated by a prime ('), and instantaneous quantity is indicated by the absence of the over-bar or prime symbols.

Combining Equations 1-4 leads to:

$$\rho_c' + \overline{\rho_c} = \rho_{cm}' \chi + \overline{\rho_{cm}} \chi \quad (5a)$$

$$\rho_c' + \overline{\rho_c} = \rho_{cm}' \chi' + \rho_{cm}' \overline{\chi} + \overline{\rho_{cm}} \chi' + \overline{\rho_{cm}} \overline{\chi} \quad (5b)$$

and computing co-variances for flux computation results in:

$$\overline{w'\rho_c'} + \overline{w'\overline{\rho_c}} = \overline{w'\rho_{cm}'\chi'} + \overline{w'\rho_{cm}'\overline{\chi}} + \overline{w'\overline{\rho_{cm}}\chi'} + \overline{w'\overline{\rho_{cm}}\overline{\chi}} \quad (6)$$

The terms where instantaneous quantity is correlated with mean quantity are cancelled, such that:

$$\overline{w'\rho_c'} = \overline{w'\rho_{cm}'\chi'} + \overline{w'\rho_{cm}'}\overline{\chi} + \overline{\rho_{cm}}\overline{w'\chi'} \quad (7)$$

and after re-arranging the order in Equation 7, the following equation is constructed:

$$\overline{w'\rho_c'} = \overline{w'\rho_{cm}'}\overline{\chi} + \overline{w'\chi'}\overline{\rho_{cm}} + \overline{w'\rho_{cm}'\chi'} \quad (8)$$

The Equation 8 is a general form of propagation of T-P effects of a single-line or narrow range laser measurement into the Eddy Covariance flux measurements.

The actual flux co-variance (left term, also referred to herein as "raw flux") is equal to measured co-variance multiplied by the mean $\chi$ (mean T-P effects over an averaging period; first term on the right), plus covariance between w' and $\chi'$ (instantaneous T-P effects; second term on the right), and co-variance of the three prime quantities (last term on the right). The last term may or may not be negligible depending on the specific form of the function $\chi = \mathcal{F}(T, P)$.

B. General Form of Full Equation for Gas Flux Computation, Including Effect of Water Dilution, Thermal Expansion, and T-P Effects.

The general form of propagation of T-P effects of a single-line or narrow range laser measurement into the Eddy Covariance flux measurements, Equation 8, can now be incorporated into full flux equation including both water dilution and thermal expansion effects (as per Ideal Gas Law) and T-P effects.

For Eddy Covariance Gas flux measurements, the Webb-Pearman-Leuning (WPL) density formulation can be written in the following form for the flux of a non-reactive gas:

$$F_c = \overline{w'\rho_c'} + \mu \frac{E}{\overline{\rho_d}} \frac{\overline{\rho_c}}{1 + \mu \frac{\overline{\rho_v}}{\overline{\rho_d}}} + \frac{S}{\overline{\rho} C_p} \frac{\overline{\rho_c}}{\overline{T}} \quad (9)$$

with water vapor flux E:

$$E = \left(1 + \mu \frac{\overline{\rho_v}}{\overline{\rho_d}}\right)\left(E_0 + \frac{S}{\overline{\rho} C_p} \frac{\overline{\rho_v}}{\overline{T}}\right) \quad (10)$$

where $F_c$ is WPL-corrected gas flux; E is WPL-corrected $H_2O$ flux; $\overline{w'\rho_c'}$ is initial $CH_4$ flux, not corrected for WPL; $E_o$ is $H_2O$ flux, not corrected for WPL; $\mu$ is ratio of molar masses of air to water ($\mu=1.6077$); $\rho_d$ is mean dry air density; $\rho_v$ is mean water vapor density; $\rho$ is mean total air mass density; S is sensible heat flux (W m$^{-2}$); $C_p$ is specific heat of air; T is gas temperature; w is vertical wind speed.

It is important to mention here, that the Webb-Pearman-Leuning density formulation (WPL) assumes that gas densities have been measured correctly, except for water dilution and thermal expansion effects as per Ideal Gas Law. So, in our terminology defined in Equations 1-3, $\rho_c$ should be used in the WPL formulation in Equation 9, and not $\rho_{cm}$.

As follows from the Equation 1, the $\overline{\rho_c} = \overline{\rho_{cm}} \overline{\chi}$. Then, combining it with Equations 8 and 9 yields:

$$F_c = \underbrace{\overline{w'\rho_{cm}'}\overline{\chi}}_{\text{1st member}} + \underbrace{\mu \frac{E}{\overline{\rho_d}} \frac{\overline{\rho_{cm}}\overline{\chi}}{1 + \mu \frac{\overline{\rho_v}}{\overline{\rho_d}}}}_{\text{2nd member}} + \underbrace{\frac{S}{\overline{\rho} C_p} \frac{\overline{\rho_{cm}}\overline{\chi}}{\overline{T}}}_{\text{3rd member}} + \underbrace{\overline{w'\chi'}\overline{\rho_{cm}}}_{\text{4th member}} + \underbrace{\overline{w'\rho_{cm}'\chi'}}_{\text{5th member}} \quad (11)$$

The Equation 11 is a full equation for gas flux computation, including effect of water dilution, thermal expansion, and T-P effects.

The first member on the right side of Equation 11 is related to raw uncorrected flux in the original WPL formulation modified due to mean T-P effects. The term $\overline{w'\rho_{cm}'}$ in the first member is sometimes referred to in the literature as the uncorrected flux in the WPL formulation, and is computed from the measured data. This term is referred to herein as "raw" flux. The term is modified according to the present invention, as expressed in Equation 11, to account for T-P effects.

Similarly, the second member is related to effect of water dilution in the original WPL formulation modified due to mean T-P effects. The term $$\mu \frac{E}{\overline{\rho_d}} \frac{\overline{\rho_{cm}}}{1 + \mu \frac{\overline{\rho_v}}{\overline{\rho_d}}}$$

in the second member is understood by those of ordinary skill to represent, with respect to the WPL formulation, the effect due to water dilution of the target gas on the measured flux of the target gas, and is a term that is computed from the measured data. This term, referred to herein generally as water dilution, is modified according to the present invention, as expressed in Equation 11, to account for T-P effects.

The third member is related to the effect of thermal expansion in the original WPL formulation modified due to mean T-P effects. The term $$\frac{S}{\overline{\rho} C_p} \frac{\overline{\rho_{cm}}}{\overline{T}}$$

in the third member is understood by those of ordinary skill to represent, with respect to the WPL formulation, a thermal expansion effect on the measured flux of the target gas, and is generally computed from the measured data. This term, referred to herein generally as thermal expansion, is modified according to the present invention, as expressed in Equation 11, to account for T-P effects.

The fourth and fifth members on the right side of the equation 11 are entirely new, and do not have equivalent terms in the original WPL formulation. These members describe instantaneous T-P effects. The latter of the two, the fifth member, may or may not be negligible depending on the form of function $\chi = \mathcal{F}(T, P)$ in the specific instrument and technique for a specific laser and gas specie.

To better understand the physical meaning of Equation 11, the equation can be re-arranged as follows:

$$F_c = \left( \overline{w'\rho'_{cm}} + \mu \frac{E}{\overline{\rho_d}} \frac{\overline{\rho_{cm}}}{1 + \mu \frac{\overline{\rho_v}}{\overline{\rho_d}}} + \frac{S}{\overline{\rho} C_p} \frac{\overline{\rho_{cm}}}{\overline{T}} \right) \overline{\chi} + \overline{w'\chi'\rho_{cm}} + \overline{w'\rho'_{cm}\chi'} \quad (12)$$

So, T-P effects propagate into flux calculation as a $\overline{\chi}$ multiplier to the traditionally computed fully corrected flux (i.e., all the members inside the parenthesis in Equation 12). This multiplier is compensated for mean T-P effects. Two additional terms $\overline{w'\chi'\rho_{cm}}$ and $\overline{w'\rho'_{cm}\chi'}$ compensate for instantaneous T-P effects.

The measured gas density $\rho_{cm}$ is a measurement that comes from the gas analyzer. The temperature and pressure for $\chi$ are obtained from the fast temperature and pressure measurement devices (either external or incorporated into the gas analyzer). The form of the $\chi$ function can be obtained from a calibration curve of the gas analyzer by performing a calibration of the instrument and/or using data from the HITRAN database or other such similar database. In general, any of a number of known techniques for calibrating an instrument can be used. Vertical wind speed typically is obtained from an anemometer. The other terms are well-known physical constants and standard atmospheric parameters.

1. Specific Derivation for the Case of the LI-7700 Methane Gas Analyzer

The LI-7700 is a methane gas analyzer developed, manufactured, and sold by the Assignee of the present invention. The LI-7700 has a measurement response (also referred to as a calibration curve or response curve or response function) that is dependent on temperature and pressure. This T-P dependence arises from a number of effects: changes in the Boltzmann population distribution of the rotational levels, Doppler and pressure broadening of individual lines. All of these effects have been calculated for the following conditions: 50 to 110 kPa (pressure range in kilopascals) and from 233K to 323K (temperature range in kelvin). These calculated absorption profiles were then run through the modulation/demodulation algorithm and the predicted responses were collected into a table. The validity of that correction table has been confirmed in controlled laboratory studies.

a) LI-7700 Instrument Calibration

The LI-7700 generates a 2F demodulated waveform of the absorption profile at some temperature and pressure. The first step in calibration is to use a zero gas to subtract any offsets to this waveform. A zero gas is flowed through the sample path. The raw data, $\overline{\alpha}_{zero}$, is recorded for 20 s. This value must be collected before spanning.

When spanning the instrument, a tank of methane/air balance is used. The mole fraction of this tank is known by the user. This gas is flowed through the LI-7700 sample path and the value of the mole fraction is entered into the software. When the calibration button is pressed, data for temperature, pressure and raw absorption is collected and used to calculate as span value. First, the gas density is calculated as follows:

$$\rho_{span} = \frac{x_{cal} R \overline{P}_{span}}{\overline{T}_{span}} \quad (13)$$

where $\rho_{span}$ is the calculated density of the calibration gas, $x_{cal}$ is the user entered mole fraction value, R is the universal gas constant, and $\overline{P}_{span}$ and $\overline{T}_{span}$ are the mean pressure and temperature calculated over 20 seconds. This density value is used to calculate a span constant:

$$C_{span} = \frac{\rho_{span}}{(\overline{\alpha}_{span} - \overline{\alpha}_{zero}) f(\overline{T}_{span}, \overline{P}_{span})} \quad (14)$$

where $C_{span}$ is the span constant, $\overline{\alpha}_{span}$ is the mean of the raw absorption calculated over 20 seconds, $\overline{\alpha}_{zero}$ is the mean of the raw absorption calculated from the zeroing procedure, and $f(\overline{T}_{span}, \overline{P}_{span})$ is a general function describing the instrument measurement response. This is given by:

$$f(\overline{T}, \overline{P}) = \frac{\rho_c}{\rho_{cm}} \quad (15)$$

where $\rho_c$ is the actual gas density and $\rho_{cm}$ is the measured gas density. Measured gas density is reported in the analyzer as follows:

$$\rho_{cm} = C_{span}(\alpha - \overline{\alpha}_{zero}) \quad (16)$$

where $\alpha$ is the instantaneous raw absorption measured on the analyzer.

b) f(T,P) Propagation Through EC Flux Measurements

The response correction function and measured and actual density can be written as the following:

$$\rho_{cm} = \overline{\rho}_{cm} + \rho'_{cm} \quad (17)$$

$$\rho_c = \overline{\rho}_c + \rho'_c \quad (18)$$

$$f(T,P) = f(\overline{T},\overline{P}) + f'(\overline{T},\overline{P})T' + H.O.T. \quad (19)$$

We can assume that the higher order terms of Taylor's expansion of f will be negligible. The function f' indicates a derivative of f and not a perturbation from the mean of f. For given instrument, water factor in T-P effects is neglected in Equation 19 in this example because of its experimentally confirmed low importance.

From equation 3, 5, and 7, the actual density is:

$$\rho_c = (\overline{\rho}_{cm} + \rho'_{cm})(f(\overline{T},\overline{P}) + f'(\overline{T},\overline{P})T') \quad (20)$$

Expanded form:

$$\rho_c = \overline{\rho}_{cm} f(\overline{T},\overline{P}) + \rho'_{cm} f(\overline{T},\overline{P}) + \overline{\rho}_{cm} f'(\overline{T},\overline{P})T' + \rho'_{cm} f'(\overline{T},\overline{P})T' \quad (21)$$

Substituting 15 and 21 into 18 and solving for gives:

$$\rho'_c = \overline{\rho}_{cm} f(\overline{T},\overline{P}) + \rho'_{cm} f(\overline{T},\overline{P}) + \overline{\rho}_{cm} f'(\overline{T},\overline{P})T' + \rho'_{cm} f'(\overline{T},\overline{P})T' - \overline{\rho}_{cm} f(\overline{T},\overline{P}) \quad (22)$$

$$\rho'_c = \rho'_{cm} f(\overline{T},\overline{P}) + \overline{\rho}_{cm} f'(\overline{T},\overline{P})T' + \rho'_{cm} f'(\overline{T},\overline{P})T' \quad (23)$$

Calculating co-variances for fluxes gives:

$$\overline{w'\rho'_c} = \overline{w'\rho'_{cm}} f(\overline{T},\overline{P}) + \overline{w'\rho_{cm}} f'(\overline{T},\overline{P})T' + \overline{w'\rho'_{cm}} f(\overline{T},\overline{P}) \quad (24)$$

For now, we will assume the 3rd term of 24 is negligible, giving:

$$\overline{w'\rho'_c} = \overline{w'\rho'_{cm}} f(\overline{T},\overline{P}) + \overline{\rho}_{cm}\overline{w'T'} f'(\overline{T},\overline{P}) \quad (25)$$

Equation 25 can now be substituted into the WPL formulation for flux shown below.

$$F_c = \overline{w'\rho'_c} + \mu \frac{E}{\overline{\rho}_d} \frac{\overline{\rho}_c}{1+\mu\frac{\overline{\rho}_v}{\overline{\rho}_d}} + \frac{S}{\overline{\rho}C_p} \frac{\overline{\rho}_c}{\overline{T}} \quad (26)$$

$$F_c = \overline{w'\rho'_{cm}} f(\overline{T},\overline{P}) + \overline{\rho}_{cm}\overline{w'T'} f'(\overline{T},\overline{P}) + \quad (27)$$

$$\mu \frac{E}{\overline{\rho}_d} \frac{\overline{\rho}_{cm} f(\overline{T},\overline{P})}{1+\mu\frac{\overline{\rho}_v}{\overline{\rho}_d}} + \frac{S}{\overline{\rho}C_p} \frac{\overline{\rho}_{cm} f(\overline{T},\overline{P})}{\overline{T}}$$

Given, $$S = \overline{\rho}C_p\overline{w'T'} \text{ or } \frac{\overline{w'T'}}{\overline{T}} = \frac{S}{\overline{\rho}C_p\overline{T}} \quad (28)$$

then Equation 27 can be arranged as:

$$F_c = \overline{w'\rho'_{cm}} f(\overline{T},\overline{P}) + \overline{\rho}_{cm} \frac{S}{\overline{\rho}C_p\overline{T}} \overline{T} f'(\overline{T},\overline{P}) + \quad (29)$$

$$\mu \frac{E}{\overline{\rho}_d} \frac{\overline{\rho}_{cm} f(\overline{T},\overline{P})}{1+\mu\frac{\overline{\rho}_v}{\overline{\rho}_d}} + \frac{S}{\overline{\rho}C_p} \frac{\overline{\rho}_{cm} f(\overline{T},\overline{P})}{\overline{T}}$$

$$F_c = \quad (30)$$

$$\overline{w'\rho'_{cm}} f(\overline{T},\overline{P}) + \mu \frac{E}{\overline{\rho}_d} \frac{\overline{\rho}_{cm} f(\overline{T},\overline{P})}{1+\mu\frac{\overline{\rho}_v}{\overline{\rho}_d}} + \frac{S}{\overline{\rho}C_p} \frac{\overline{\rho}_{cm}}{\overline{T}} [f(\overline{T},\overline{P}) + \overline{T} f'(\overline{T},\overline{P})]$$

This form of the flux equation allows for the use of a general function for the measure response of the LI-7700 instrument to be applied to half hour data rather than on instantaneous data. The derivative of f can be computed very easily from curve fits to the T-P curve or numerically from table values.

Validation of the Proposed Method Using LI-7700 Methane Analyzer and Field Data

The general equations 8 and 11 and instrument-specific equations 24 and 30 were validated on the example of LI-7700 fast methane analyzer (2009 version of instrument and methodology of scanning methane line). The form of $\chi$ in this example is shown in a normalized form in FIGS. 5A and 5B using linear (FIG. 5A) and exponential (FIG. 5B) fits. For a given instrument, water factor in T-P effects is neglected in this example because of its experimentally confirmed low importance.

Using linear fit in this specific example, the $\chi$ can be approximated as follows:

$$\chi \approx 0.32\frac{T}{\overline{T}} + 0.67 \quad (31)$$

$$\overline{\chi} \approx 0.32\frac{\overline{T}}{\overline{T}} + 0.67 = 0.99 \quad (32)$$

$$\chi' \approx \left(0.32\frac{T}{\overline{T}} + 0.67\right)' = \frac{0.32}{\overline{T}} T' \quad (33)$$

Combining Equations 11 and 32-33 yields:

$$F_c = 0.99\overline{w'\rho'_{cm}} + 0.99\mu \frac{E}{\overline{\rho}_d} \frac{\overline{\rho}_{cm}}{1+\mu\frac{\overline{\rho}_v}{\overline{\rho}_d}} + \quad (34)$$

$$0.99\frac{S}{\overline{\rho}C_p} \frac{\overline{\rho}_{cm}}{\overline{T}} + \frac{0.32}{\overline{T}} \overline{w'T'\rho_{cm}} + \frac{0.32}{\overline{T}} \overline{w'\rho'_{cm}T'}$$

The right most member of the equation 34 becomes negligible, because the product is several orders of magnitude smaller than other members, yielding:

$$F_c = 0.99\overline{w'\rho'_{cm}} + 0.99\mu \frac{E}{\overline{\rho}_d} \frac{\overline{\rho}_{cm}}{1+\mu\frac{\overline{\rho}_v}{\overline{\rho}_d}} + 0.99\frac{S}{\overline{\rho}C_p} \frac{\overline{\rho}_{cm}}{\overline{T}} + \frac{0.32}{\overline{T}} \overline{w'T'\rho_{cm}} \quad (35)$$

Finally, using standard equation for sensible heat flux, $S = \overline{\rho}C_p\overline{w'T'_a}$, the equation 35 becomes:

$$F_c = 0.99\overline{w'\rho'_{cm}} + 0.99\mu \frac{E}{\overline{\rho}_d} \frac{\overline{\rho}_{cm}}{1+\mu\frac{\overline{\rho}_v}{\overline{\rho}_d}} + 1.31\frac{S}{\overline{\rho}C_p} \frac{\overline{\rho}_{cm}}{\overline{T}} \quad (36)$$

The Equation 35 is a specific sub-case of Equation 30 for given atmospheric pressure and given calibration temperature and pressure, while Equations 30 is a specific sub-case of Equation 11 for given instrument. It describes propagation of both T-P effects and density effects (per Ideal Gas Law) into the Eddy Covariance flux calculations using LI-7700 gas analyzer.

Using exponential fit instead of linear fit (Eqs. 31-33) in this specific example, the function $\chi$ can be approximated as follows:

$$\chi \approx 0.712\exp\left(0.323\frac{T}{\overline{T}}\right) \quad (37)$$

$$\overline{\chi} \approx 0.712\exp\left(0.323\frac{\overline{T}}{\overline{T}}\right) = 0.98 \quad (38)$$

$$\chi' \approx 0.712 * \frac{0.323}{\overline{T}} * T'\exp\left(0.323\frac{T}{\overline{T}}\right) = \quad (39)$$

$$\frac{0.23}{\overline{T}} T'\exp\left(0.323\frac{T}{\overline{T}}\right) \approx \frac{0.23}{\overline{T}} T'\exp(0.323) = \frac{0.32}{\overline{T}} T'$$

Either linear or exponential fit yield substantially same results, with identical $\chi'$ and similar $\chi$-means. The 1% difference in $\chi$-means is likely due to an imperfections of linear fit over the wide range of temperatures (−40 to +50° C.).

Since forms of Equations 31 or 37 vary in LI-7700 (2009 version of instrument and methodology of scanning methane line) with actual and calibration gas temperatures and pressures, the fitting is not the preferable approach in this case. High-resolution look-up table would provide a more accurate value of $\chi$ for every specific time and set of conditions.

Figure 6:
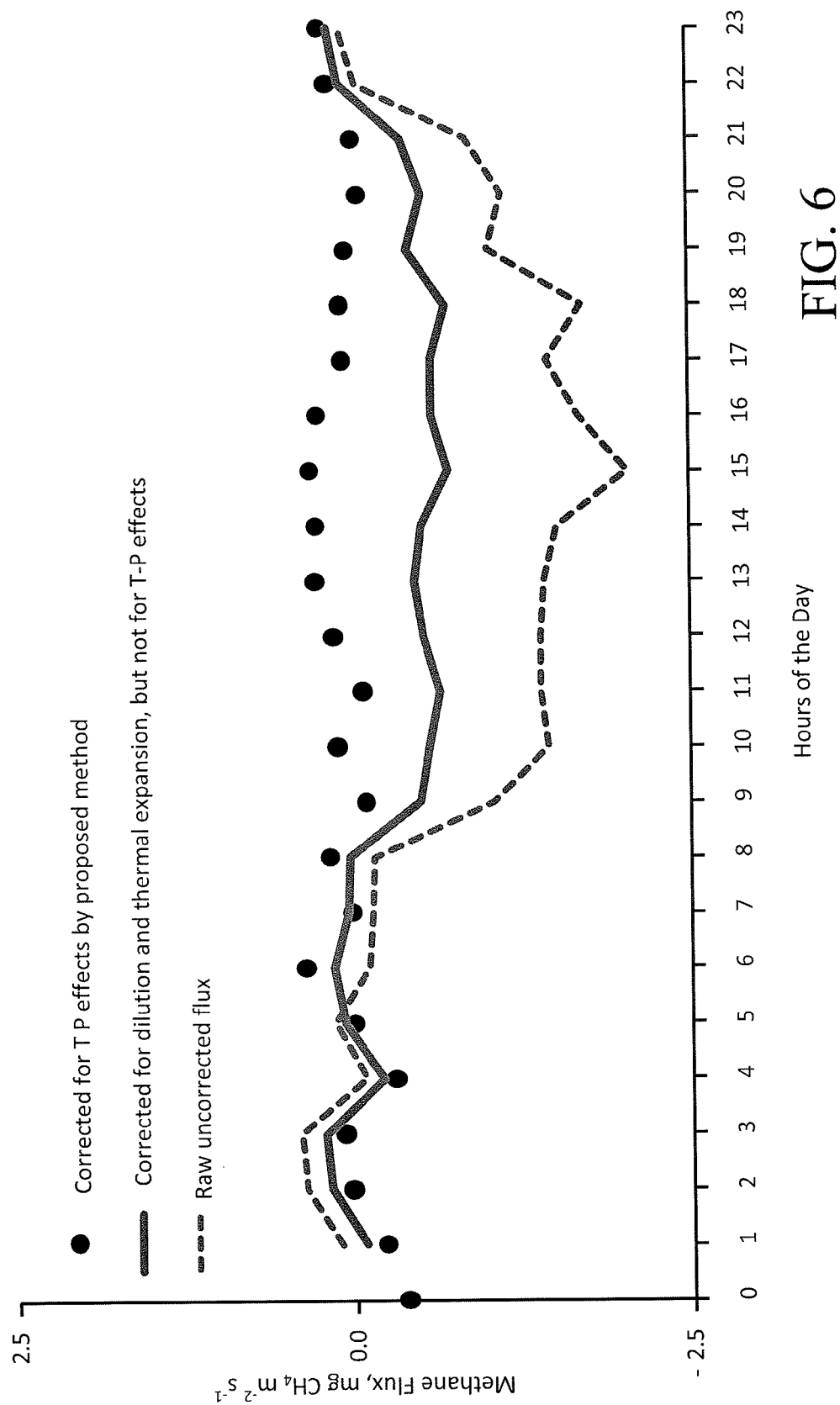
FIG. 6 represents results from actual test data, comparing conventional determinations of flux with determination of flux per the present invention.

To validate Equations 11, 30 and 36, it is convenient to compare methane fluxes from the non-producing field site with and without the correction for T-P effect. FIG. 6 illustrates such a test, showing an ensemble of averaged flux data from two weeks in the Summer of 2009, over an agricultural field in Mead, Nebr.

The experimental site had a long history of chamber measurements of very small $CH_4$ fluxes (−0.1 to 0.1 mg/m$^2$ per hour, year round). As seen in FIG. 6, when the proposed method is not used to correct the measured flux, the measurements are incorrect, exceeding the expected range of fluxes by up to 10 times. When the proposed method is used, the measurements become not significantly different (standard error on each point is about 0.19 mg/m$^2$ per hour) from the numbers measured by chambers. This is strong evidence that the method in accordance with the present invention works correctly.

The discussion will now turn to a description of FIG. 1. The figure illustrates several elements of an example of a gas analysis system according to the present invention. Those of ordinary skill will appreciate that the system shown in FIG. 1 may include additional elements not shown in the figure. However, it is not necessary that all of these generally conventional elements be shown in order to disclose an illustrative embodiment for practicing the present invention.

The illustrative gas analysis system shown in FIG. 1 can be viewed as comprising two sub-systems: a measurement sub-system 122 and a data and control sub-system 124. A data communication component 126 allows data and control information to be communicated between the two sub-systems 122, 124. The data communication component 126 can use any of a number of conventionally known data communication techniques. The data communication component 126 can be wireless. This would be preferable if the measurement sub-system is at a location that is remote, or otherwise not readily accessible, from the personnel (scientists, engineers, etc) who are collecting the data. Examples of wireless configurations, include for example, a radio frequency communication link, an optical communication link, and so on. The data communication component 126 can comprise hardwired ("wired") connections such as ethernet cabling, RS-232 communication using a modem, high speed connection (USB, firewire, etc.) to a data logging device, or any other suitable wired configuration. Finally, the data communication component 126 can be some combination of wired and wireless communication, depending the specific configurations of the elements of the gas analyzer system.

FIG. 1 shows that the data communication component 126 includes a plurality of data/communication lines that connect each instrument in the measurement sub-system 122 to the control sub-system 124. The illustrated data/communication lines can be physical wires/cabling, or a form of wireless communication link (e.g., radio), or some combination of both. In the configuration shown, each instrument in the measurement sub-system 122 communicates with the data and control sub-system 124. Alternatively, two or more of the instruments can be connected together in serial fashion (e.g., daisy chained) and communications with the data and control sub-system 122 can occur over a single communication line.

The measurement sub-system 122 includes a gas analyzer 102, a wind speed measuring device 104, a water vapor analyzer 106, and a temperature sensor 108. The gas analyzer 102 is any conventionally known analyzer suitable for measuring the density of a target gas; i.e., the gas of interest that is to be analyzed. For example, methane ($CH_4$) is a commonly measured gas and methane analyzers for measuring methane density are commercially available, such as the LI-7700 Open Path $CH_4$ Analyzer, designed, manufactured, and sold by the assignee of the present invention. Generally, absorption based gas analyzers use absorption of light from either (i) a broadband non-dispersive infrared (NDIR) source equipped with suitable optical filter or (ii) a narrowband laser source to measure the density of the target gas of interest. The light is selectively absorbed by the gas as it crosses the light path between the light source and a detector in a region called the sampling volume (also variously referred to as "sample volume," "sampling path," and so on)." The gas analyzer 102 outputs gas density measurement data based on the measured absorption characteristics. Two categories of gas analyzers are conventionally known which are defined by the nature of the sampling volume. An "open path" type gas analyzer is one in which the sampling volume and the optical path are exposed to the environment containing the gas to be analyzed. A "closed path" gas analyzer is one in which the sampling volume is enclosed in a tube (in which case the sampling volume can be referred to as the sample cell) and the optical path lies within the tube, and the gas to be measured is passed within the tube. In accordance with the present invention, the gas analyzer 102 can be either an open path analyzer or a closed path analyzer or a combination of the two. For example, U.S. Pat. Nos. 6,317,212 and 6,369,387, each of which is hereby incorporated by reference in its entirety, disclose various features of open and closed path gas analyzers.

The wind speed measuring device 104 produces a measure of the speed of the moving air in the vicinity of the gas analyzer 102 and outputs corresponding wind speed measurement data. More specifically, the wind speed measurement in accordance with the present invention is vertical wind speed. An instrument commonly used to measure wind speed is known as a sonic anemometer. This instrument is commonly used with open path gas analyzers. There are several types of sonic anemometers, ranging in complexity. The most basic models of sonic anemometers measure the wind speed, while the more complex ones can measure wind speed, wind direction, and wind pressure. It will be appreciated of course that other wind speed measurement devices and techniques can be used.

The water vapor analyzer 106 provides a measure of the water content of the target gas and produces a series of water vapor measurement data. As explained above, the amount of light absorption by the target gas is affected by temperature and pressure. Water vapor analyzers are commercially available, and any such commercially available analyzer can be used with embodiments of the present invention. An example of a suitable water vapor analyzer 106 is the LI-7200 $CO_2$/$H_2O$ Analyzer, designed, manufactured, and sold by the assignee of the present invention.

In certain environments, the water content can be significant enough to considerably affect the absorption lineshape of the target gas and the resulting density measurement. Dilution by water vapor causes an actual physical change in partial pressure and a change in actual density when compared to dry. In addition, water vapor affects absorption by line broadening which consequently affects the resulting density measurement. Under such conditions, more accurate results will be achieved if the water content is measured and factored into the computations. However, if the environment where the target gas is being analyzed is sufficiently dry, the water content may not have any significant affect on density measurements of the target gas. In that case, the cost and complexity of coordinating gas density measurements with water vapor measurements can be dispensed with and the water vapor analyzer 106 would not be required to correct for T-P effects.

The temperature sensor 108 is used to measure ambient temperature in the proximity of the gas density measurements. Typical devices for the temperature sensor 108 include a fine-wire thermocouple, a sonic anemometer, and in general any device that can provide fast gas temperature measurements. In accordance with the present invention, the temperature sensor 108 can be positioned in proximity to the sampling volume of the gas analyzer 102, or alternatively within the sampling volume.

The data and control sub-system 124 includes a suitable data processing component 112, data storage 114, and a suitable user interface 116. Those of ordinary skill in the art will appreciate that the data and control sub-system 124 may include many more components than those shown in FIG. 1. However, it is not necessary that all of these generally conventional components be shown in order to disclose an illustrative embodiment for practicing the present invention.

Typical devices that can serve as the data storage 114 include traditional disk storage devices such as hard disk drives, floppy disk drives, writable CD-ROMs, other removable storage formats, and the like. Data storage 114 can also include flash memory devices such as flash drives, or other similar static storage devices. Data storage 114 is typically a high capacity storage device for storing the large amounts of measurement data that can be obtained from the measurement sub-system 122 during a data collection session. The data storage 114 may be called upon to store data from several data collection sessions.

The user interface 116 broadly covers various mechanisms for user input and output, and collectively refers to any combination of suitable user input devices and output or display devices. The "user" can be a human user, or a machine user. In the case of a machine user, the interface 116 can any suitable analog or digital communication interface for communication with another computing machine that is configured to operate the gas analysis system of FIG. 1 by interfacing with the data and control sub-system 124. In the case of a human user, the interface 116 can include input devices such as a mouse pointing device, a keyboard, a graphics tablet, a touch screen device, and so on. The interface 116 can further include output devices such as a video display monitor, a simple set of LED indicators, a printing device, a removable flash memory device (e.g., USB thumb-drive), and so on. The interface allows the user to control the data and control sub-system 124 to configure the measurement sub-system to 122 to collect measurements and to store the measurements in the data storage 114.

The data and control sub-system 124 can be configured to any level of sophistication as needed for a particular implementation of the gas analysis system of FIG. 1, and typically is built to survive rugged field deployments for months or even years on end. The data and control sub-system 124 can be a simple data logging component configured to communicate with the measurement sub-system 122 to simply receive data to be stored in the data storage 114. Examples of such a data and control sub-system 124 include devices variously referred to in the industry as data loggers; as measurement and control units, microloggers, and so on. Such devices can measure the instruments at a specific scan rate, process data, and store the data.

In accordance with the present invention, the data and control sub-system 124 can be a more full-featured and sophisticated data logging component that is not only able to communicate with the measurement sub-system 122 and receive measurement data from the measurement sub-system to be stored in the data storage 114, but also includes computer program code in accordance with the present invention to produce temperature and pressure corrected gas flux values of the target gas of interest. It is noted that the data and control sub-system 124 need not be near the measurement sub-system. In fact, depending on the particular usage scenario of the present invention, the two sub-systems 122, 124 can be quite distant from each other.

Figure 2:
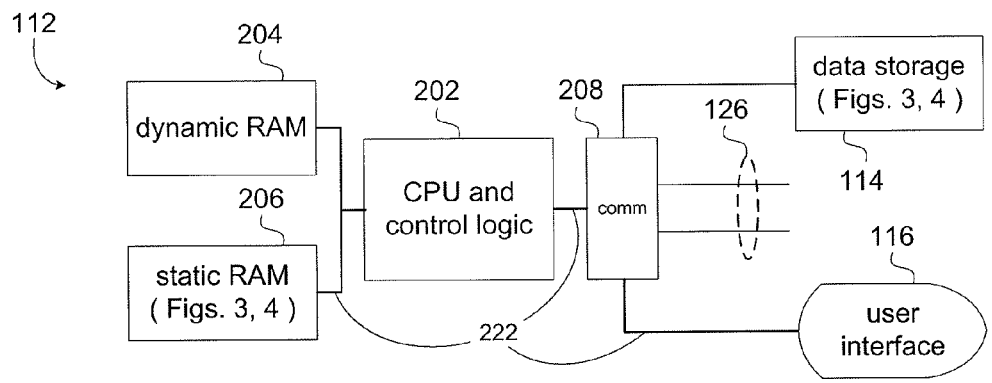
FIG. 2 shows a system block diagram of a typical embodiment of a data handling system in accordance with the present invention.

Referring now to FIG. 2, the data processing component 112 of the data and control sub-system 124 comprises a conventional data processor 202, for example, a central processing unit or a microcontroller or a combination of both, connected to other constituent components via the data and control bus lines 222. The data processor 202 can be, or includes, a programmable logic device (PLD) or a field programmable gate array (FPGA), or other similar and commonly known logic devices. Those of ordinary skill in the art will appreciate that the data processing component 112 may include many more components than those shown in FIG. 2. However, it is not necessary that all of these generally conventional components be shown in order to disclose an illustrative embodiment for practicing the present invention.

The data processing component 112 includes memory components 204, 206. The static memory component 206 is typically used to store the various computer programs (e.g., operating system, applications) that are executed by the data processor 202. Typical static memories include programmable read-only memory (PROM), flash RAM, and so on. Computer program instructions (or computer code) in accordance with the present invention (explained with respect to FIGS. 3 and 4 below) can be stored in the static memory 207. One of ordinary skill in the art will appreciate that when the computer program instructions are executed by the data processor 202, different portions of the computer program instructions may be loaded into the dynamic memory 204; e.g., random access memory (RAM). One of ordinary skill will further appreciate that computer program instructions can be stored in the data storage device 114. The individual memories 204, 206 and the data storage 114 illustrate various forms of computer-readable storage media. Depending on the particular configuration, it will be appreciated that the computer program instructions according to the present invention can be stored for execution by the data processor 202 entirely on one of memories 204, 206 or data storage 114, or distributed among the memories 204, 206 and data storage 114.

The data processing component 112 further includes a communication interface 208 which provides the circuitry and logic, including electrical and/or optical components, for communications with the measurement sub-system 122. The communication interface 208 also includes circuitry and logic for connecting to the data storage 114 and the user interface 116. The communication interface 208 includes analog and digital circuitry to perform data acquisition in order to collect data from the suite sensors that constitute the measurement sub-system 122. In a particular embodiment, such data acquisition circuitry can be embodied in a separate component commonly referred to as a data acquisition card.

Figure 3:
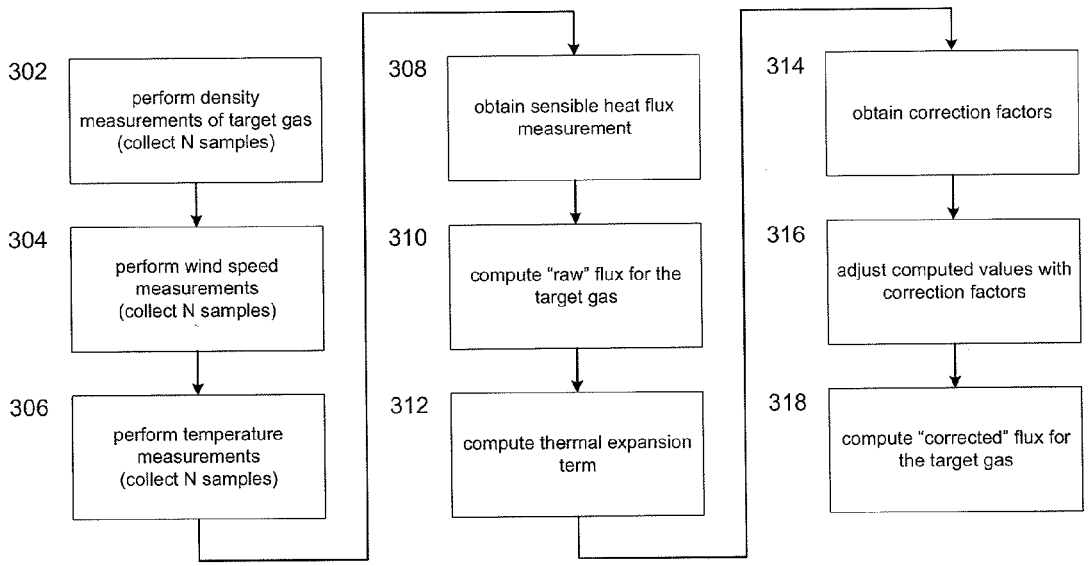
FIG. 3 shows the processing for determining flux values corrected for temperature and pressure in accordance with one embodiment of the present invention.
Figure 4:
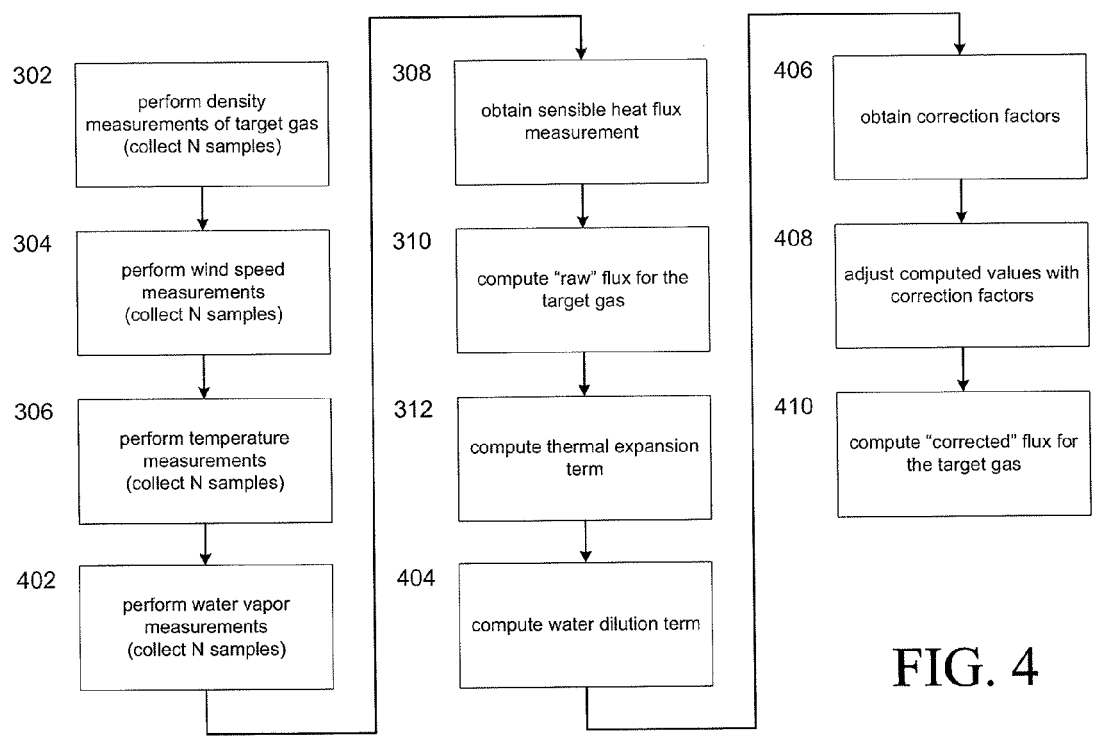
FIG. 4 shows the processing for determining flux values corrected for temperature and pressure in accordance with another embodiment of the present invention.

Referring now to FIGS. 3 and 4, a discussion of the computer program code in accordance with the present invention for computing gas flux for a target gas that is corrected for temperature and pressure conditions. The program code will be explained in terms of the flowcharts illustrated in the figures rather than in terms of actual lines of program code, since the later would include details not relevant to the discussion of the invention. The flowcharts in FIGS. 3 and 4 are almost the same, with the exception of measurements for water vapor in FIG. 4. FIG. 3 illustrates a situation where water content in the target gas is not significant, while FIG. 4 covers the more general situation where water content in the target gas is considered.

The computer program code is typically executed by the data processor 202 (e.g., a CPU or a microcontroller). Typically, the computer program code includes computer instructions, also known as machine language, that cause the data processor to perform various control operations and data manipulation operations. In addition, to traditional machine code language that is executed by physical central processing units (e.g., Intel processors, Texas Instruments microcontrollers, and the like), the computer instructions can be provided for so-called "virtual machines." A popular example is the Java programming language which can be compiled to produce "bytecode" that runs on a Java virtual machine (JVM). This and other alternatives to traditional CPU architectures can be readily accommodated in accordance with the present invention. The flowcharts in FIGS. 3 and 4 represent high-level processing steps in accordance with the disclosures of the present invention. One of ordinary skill in the art will readily appreciate that the flows (e.g., FIGS. 3 and 4) can be implemented for a specific data processor or data processors in myriad ways, including but not limited to the data processor 202. For example, if the data processor 202 includes one or more PLD, FPGA, or some other similar kind of logic device, then it will be appreciated by those of ordinary skill in the that some or all of the processing (e.g., FIGS. 3 and 4) may be implemented in such logic device(s).

Referring to the particular flow shown in FIG. 3, the process begins with data collection steps 302-308. In step 302, the gas analyzer 102 operates to perform a series of measurements of gas density of the target gas. A series of gas density measurement data are produced by the gas analyzer 102, and obtained by the data processor 202 to be stored in data storage 114. In step 304, the wind speed measuring device 104 operates to perform a series of measurements to measure the wind speed during the same time that the gas density measurements are being performed. The series of wind speed measurement data that is produced is obtained by the data processor 202 and stored in data storage 114. In step 306, a series of measurements are performed by the temperature sensor 108 to obtain temperature measurement data which are then stored in data storage 114.

The data collection rate is typically on the order of 10 Hz or so; i.e., 10 Hz means 10 samples are collected per second. The sampling rate can be higher or lower as ambient conditions require and/or depending on the measurement devices. For example, in order to compute gas flux using the Eddy Covariance technique (or using other similar techniques), the instrument needs to sample all relevant air parcels traveling up and down. If the instrument is too slow, then it will miss flux transport in small and fast movements. Typically, people collect data at rates of 10-20 times per second. An advantageous aspect of the present invention is that the low end of the range of data collection rates can be very low (e.g., 5 Hz) while still allowing correct flux determinations. Thus, for closed path or open path systems with very tall towers, the data collection rate can be 5 times per second and still measure flux correctly because the higher you go the bigger and slower the motions are involved in most of the air and gas transport. When people measure with airplanes, they may go to 40 Hz or more due to fast travelling through these motions.

Typically, the data collection rate for each measurement (gas density, wind speed, temperature) is the same. Thus, for a data collection rate of 10 Hz that means ten gas density measurements are taken per second and stored, and ten wind speed measurements and ten temperature measurements are taken per second and stored. However, it is possible to collect the different kinds of measurements at different rates. For example, the gas density measurements can be collected at say 30Hz, while the wind speed measurements are collected at 40 Hz and the temperature measurements are collected at 50 Hz. However, the foregoing analytical techniques require that the measurements be correlated with wind speed. Thus, using conventionally known digital data processing techniques, such sub-sampling or averaging, the wind speed can be sub-sampled into 30 Hz data in order for the gas density data to be correlated with the wind speed data. Likewise, the temperature data can be sub-sampled down to 40 Hz data in order for the temperature data to be properly correlated with the wind speed data.

In step 308, a sensible heat flux value is obtained. This particular embodiment of the present invention is suitable for ambient conditions that are sufficiently dry so as not to require taking water vapor measurements. Since sensible heat flux is typically computed based on water vapor measurements, for this particular embodiment, where there are no water vapor measurements, the sensible heat flux can be obtained by taking measurements using a scintillometer or a LIDAR, or can estimated from known and conventional modeling techniques using solar radiation, soil moisture, etc.

Steps 302-308 in FIG. 3 relate to collecting, modeling (in the case of sensible heat flux), or otherwise obtaining some of the measurements used in the analytical techniques of the present invention. The remainder of FIG. 3 relates to the analytical techniques to determine a corrected gas flux of the target gas. Reference will be made to the equations and derivations discussed above.

In step 310, a "raw" uncorrected flux value $\overline{w'\rho_{cm}'}$ is computed from the gas density measurements obtained in step 302. The raw flux is a value computed based on the measured data, as discussed in connection with Equation 11 above. As explained, the raw flux is $\overline{w'\rho_{cm}'}$, where w' is the deviation of a wind speed measurement from the mean (average) value of all of the vertical wind speed measurements. The term $\overline{w'}$ represents the average of all such deviations. Similarly, $\rho_{cm}'$ is the deviation of a gas density measurement of the target gas (e.g., methane) from the mean (average) value of all of the gas density measurements, and the term $\overline{\rho_{cm}'}$ represents the average of all such deviations. The particular mathematical expression for the uncorrected flux will vary depending on the particular method of calculating the flux.

In step 312, a thermal expansion term is computed from the measurements obtained in steps 302-308. The thermal expansion term $$\frac{S}{\overline{\rho}C_p}\frac{\overline{\rho_{cm}}}{\overline{T}}$$

represents the effect of thermal expansion effect on the measured flux of the target gas in connection with the WPL formulation for flux calculations. The terms are explained above. It will be appreciated by one of ordinary skill in the art that this thermal expansion term is not unique to the WPL formulation, but rather is a term that represents the thermal expansion effects on gas flux due to heat flux, and is a term that is present in most models. The particular mathematical expression of the thermal expansion term, however, will vary depending on the parameters of the specific model.

In step 314, correction factors are determined in accordance with the present invention as discussed above in connection with the equations above. In particular, Equation 11 represents the most general form and accounts for all temperature and pressure effects on gas absorption lines upon which gas density measurements are made. Equation 30, shows an example of compensating for the effect of temperature and pressure on the measurement response of a specific instrument; e.g., the LI-7700 gas analyzer of the assignee of the present invention. Equation 36 is a specific instance of Equation 30, determined for a given pressure value and a range of temperatures. Since the discussion of FIG. 3 assumes the effect of water dilution is negligible and thus being ignored, the water dilution term in Equations 11, 30, and 36, namely $$\mu \frac{E}{\overline{\rho_d}} \frac{\overline{\rho_{cm}}}{1+\mu \frac{\overline{\rho_v}}{\overline{\rho_d}}},$$

can be dropped out of the equations.

An example of the correction factors is shown in Equation 36 as the coefficients of the terms $\overline{w'\rho_{cm}'}$ and $$\frac{S}{\overline{\rho} C_p} \frac{\overline{\rho_{cm}}}{\overline{T}}$$

from steps 310 and 312, namely 0.99 and 1.31. These coefficients were obtained by considering the response function of the specific instrument used to measure gas density, and in particular the response function at the same pressure as when gas density was measured. A discussion of the determination of the specific coefficient values shown in Equation 36 is explained in connection with Equations 31-35 above.

Typically, the response function is calculated using specific spectroscopic parameters from the HITRAN database and experimentally validated by taking a series of gas density measurements over a range of temperatures at a given density of the target gas at a given pressure. The HITRAN (High Resolution TRANsmission Molecular Absorption Database) database is a recognized international standard publically available compilation of spectroscopic reference data. Of course, sources for spectroscopic reference data other than the HITRAN database can certainly be used. In addition, as another source of spectral data, there are a variety of open source software, web based simulations, and the like that allow a person to run any simulations using a complete set of parameters. Also, it will be appreciated that any of a number of known techniques for calibrating an instrument can be used.

Figure 5A:
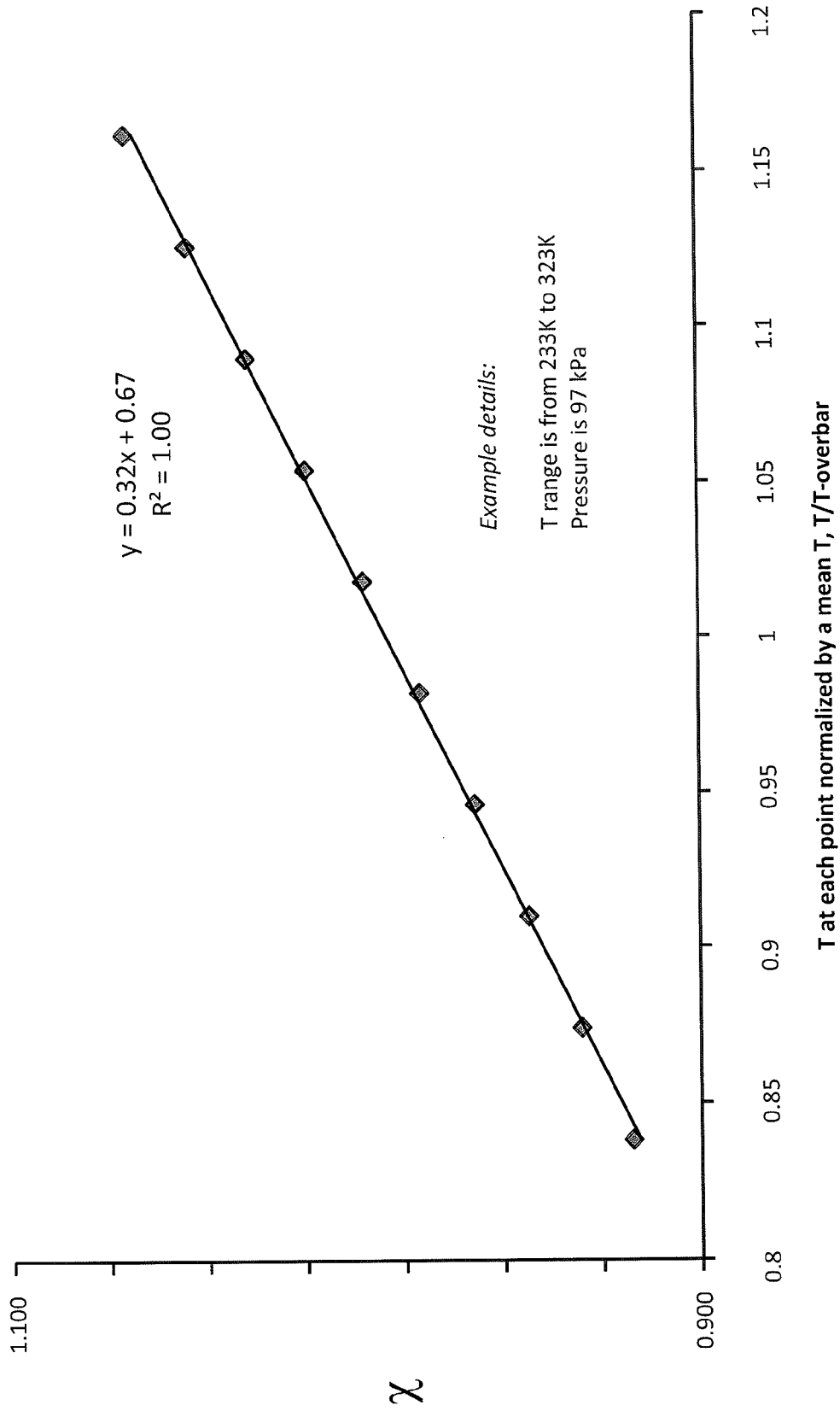
FIGS. 5A and 5B show calibration curves for a gas analyzer.
Figure 5B:
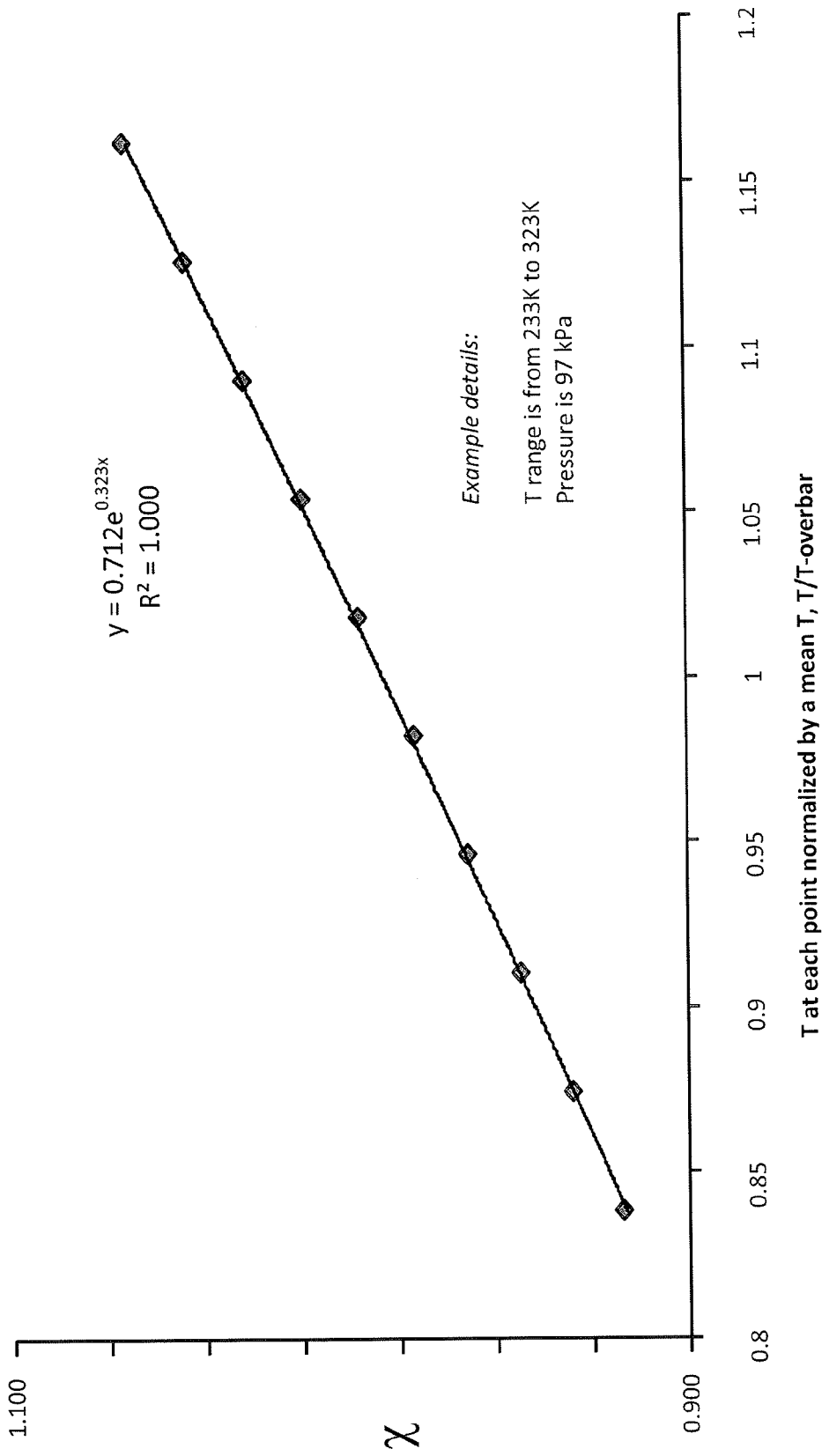

FIG. 5A illustrates an example of the result of such calculations fitted with a linear approximation to obtain the calibration curve shown in the figure. FIG. 5B shows the same data fitted with an exponential model. This data was calculated at a given pressure; e.g. 97 kPa (kilopascals) over a temperature range from 233K to 323K (kelvin). The horizontal axis is a normalized temperature scale where the temperature range is normalized by the mean temperature ($\overline{T}$, T-over-bar). The vertical axis is a value of the $\chi$ function at a specific temperature and pressure.

A calibration "surface" (response surface) is obtained if one obtains several calibration curves by repeating the foregoing calculations or/and data collection for several values of pressure. The calibration surface then can be used to select an appropriate calibration curve based on the pressure under which the measurements (steps 302-308) were obtained. The selected calibration curve is then used to determine the coefficients for Equation 36, as explained in connection with Equations 31-35, or alternatively in connection with Equations 37-39.

In step 316, the terms obtained in steps 310 and 312 are adjusted by the correction factors obtained in step 314. In the particular embodiment per Equation 36 of the present invention, the coefficients 0.99 and 1.31 are multiplied respectively with the terms $\overline{w'\rho_{cm}'}$ and $$\frac{S}{\overline{\rho} C_p} \frac{\overline{\rho_{cm}}}{\overline{T}}.$$

The corrected flux $F_c$ is then computed (step 318) in accordance with Equation 36 by summing the adjusted terms, specifically in the case where water dilution is not a significant effect and can be ignored, the corrected flux is:

$$F_c = 0.99 \overline{w'\rho_{cm}'} + 1.31 \frac{S}{\overline{\rho} C_p} \frac{\overline{\rho_{cm}}}{\overline{T}}.$$

Referring now to FIG. 4, recall from the introductory discussion above of FIGS. 3 and 4, that unlike FIG. 3, FIG. 4 represents a scenario where the effects of water content in the target gas cannot be ignored. The steps in FIG. 4 common to those in FIG. 3 are identified with the same reference numerals and their discussion need not be repeated here. In FIG. 4, there is an additional measurement, namely the water vapor measurements, step 402. In step 404, a water dilution term is computed from the measurements obtained in steps 302-308, 402. The water dilution term $$\mu \frac{E}{\overline{\rho_d}} \frac{\overline{\rho_{cm}}}{1+\mu \frac{\overline{\rho_v}}{\overline{\rho_d}}}$$

represents latent heat flux effect (due to the presence of water vapor in the target gas) on the measured flux of the target gas in connection with the WPL formulation for flux calculations. It will be appreciated by one of ordinary skill in the art that the above water dilution term is not unique to the WPL formulation, but rather is a term that represents the effect on the target gas flux due to water content in the target gas that is modeled by most models. The particular mathematical expression of the water dilution term, however, will vary depending on the parameters of the specific flux model.

In step 406, the correction factors are computed as explained above in FIG. 3 for step 314. Since water vapor effects are being considered, the discussion of Equations 34-36 include the effects of water dilution, namely the term $$\mu \frac{E}{\overline{\rho_d}} \frac{\overline{\rho_{cm}}}{1+\mu \frac{\overline{\rho_v}}{\overline{\rho_d}}}.$$

In step 408, the terms obtained in steps 310, 312, and 408 are adjusted by the correction factors obtained in step 406. In the particular embodiment per Equation 36 of the present invention, the coefficients 0.99, 099, and 1.31 are multiplied respectively with the terms $\overline{w'\rho_{cm}'}$, $$\mu \frac{E}{\overline{\rho_d}} \frac{\overline{\rho_{cm}}}{1+\mu\frac{\overline{\rho_v}}{\overline{\rho_d}}}, \text{ and } \frac{S}{\overline{\rho}C_p}\frac{\overline{\rho_{cm}}}{\overline{T}}.$$

The corrected flux $F_c$ is then computed (step 410) in accordance with Equation 36 by summing the adjusted terms.

In the discussion that follows, it is assumed that barometric pressure is measured and constant. To date, the flux measurement community assumes high frequency pressure fluctuations can be neglected in Eddy Covariance measurements. For this reason, the method to be described here neglects such fluctuations. However, it will be apparent that the method can be extended to include high frequency pressure fluctuations if such are found to be important for gas measurements using the Eddy Covariance technique.

Pressure Broadening Effect of Diluent Gases

For the case when T-P effects consist of broadening due to temperature, pressure and water vapor, $\chi=\chi(T,P,\rho_v)$. The effects of pressure broadening and diluent gas broadening (e.g., water vapor broadening) can be represented with a single quantity called equivalent pressure, $P_e$ (Pa). All gases are not equally effective in causing pressure broadening of absorption lines. In one embodiment, this is accounted for using the concept of equivalent pressure, $P_e$. Equivalent pressure is defined as $P_e = \rho_{N2} + \Sigma a_i p_i$ where $\rho_{N2}$ is the partial pressure of nitrogen, and $\rho_i$ gives the partial pressures of other diluent non-absorbing gases, each multiplied by a foreign gas coefficient $a_i$. The coefficients $a_i$ reflect the ability of each diluent gas to cause pressure broadening relative to broadening caused by $N_2$. The discussion below will focus on water vapor as the diluent gas, however, the discussion is equally applicable to any foreign gas that acts as a diluent gas.

Measurements are typically made in air where water vapor is the only variable component in sufficient concentration to affect broadening. Therefore, in one aspect, $P_e$ is defined relative to dry air instead of nitrogen, so $P_e = \rho_d + a_v\rho_v$, where $\rho_d$ is partial pressure of dry air (Pa), $a_v$ is the foreign gas broadening coefficient for water vapor relative to dry air, and $\rho_v$ is water vapor partial pressure (Pa). Total pressure P can be written as $P=\rho_d+\rho_v$. Subtracting P from $P_e$ and rearranging gives $P_e=P(1+\alpha_v x_v)$, where $\alpha_v=a_v-1$, and $x_v=\rho_v/P$ is water vapor mole fraction. For the LI-7700, $a_v$ is found experimentally to have a value of 1.46, but this value may vary for other instruments depending upon the gas species, the absorption line or lines being measured, and the instrument design.

Using the Ideal Gas Law, $P_e$ also can be re-written as $P_e=P+\alpha_w RT\rho_v$, where $\rho_v=p_v(RT)^{-1}$ is water vapor number density (mol m$^{-3}$). Now we can view the effects of water vapor as a perturbation on the total pressure, so $\chi=\chi(T, P, \rho_v)$ can be rewritten as $\chi=\chi(T, P_e)$.

Different expansion or decomposition techniques can be used to approximate the values of (1). Modification of above equations to include equivalent pressure follows. Using a Taylor series expansion for $\chi$, and Reynold's decomposition for $\rho_c$ and $\rho_{cm}$, each term can be written as follows:

$$P_c = \overline{P_c} + P_c' \quad (2')$$

$$P_{cm} = \overline{P_{cm}} + P_{cm}' \quad (3')$$

$$\chi = \chi(\overline{T},\overline{P_e}) + \chi_T(\overline{T},\overline{P_e})\delta T + \chi_{Pe}(\overline{T},\overline{P})\delta P_e + H.O.T., \quad (4')$$

where $$\chi_T = \frac{\partial \overline{\chi}}{\partial T} \text{ and } \chi_{Pe}\frac{\partial \overline{\chi}}{\partial Pe}.$$

The terms $\delta T$ and $\delta P_e$ can be approximated as T' and $P_e'$ respectively. For simplicity, $\chi(\overline{T},\overline{P_e})$ will be denoted as $\overline{x}$ for the rest of the document. Mean quantities are denoted by the over-bars. The deviation of instantaneous quantity from the mean is indicated by a prime. Instantaneous quantity is indicated by the absence of over-bar or prime.

Expanding equation 1 with equations 2'-4' leads to:

$$\overline{\rho_c}+\rho'_c=(\overline{\rho_{cm}}+\rho_{cm}')(\overline{\chi}+\chi_T T'+\chi_{Pe}P_e') \quad (5')$$

$$\overline{\rho_c}+\rho'_c=\overline{\chi\rho_{cm}}+\overline{\chi}\rho'_{cm}+\chi_T T'\overline{\rho_{cm}}+\chi_T t'\rho'_{cm}+\chi_{Pe}P_e' \overline{\rho_{cm}}+\chi_{Pe}P_{e'}\rho'_{cm} \quad (6')$$

From equation 1 with $\overline{\rho_c}=\overline{\rho_{cm}}\chi$, the first terms on the left side and right side of equation 6' cancel. Furthermore, the double prime terms can be approximated as 0, since the covariance of double prime terms with w' have been found experimentally to be negligibly small; however, this may not always be the case and they can be carried through the derivation, if needed. But making this assumption in the present case, and computing co-variances w' for flux results in:

$$\overline{w'\rho'_c}=\overline{\chi}\overline{w'\rho'_{cm}}+\chi_T\overline{w'T'\rho_{cm}}+\chi_{Pe}\overline{w'P_e'\rho_{cm}} \quad (7')$$

where flux $(w'\rho'_c)$ is in mol m$^{-2}$ S$^{-1}$. $P_e'$ in equation 7' can be rewritten in terms of $\rho'_v$, or water vapor density, since $P'_e=\alpha_v R T\rho_v''$ Substituting $$R\overline{T} = \frac{\overline{P}}{\overline{\rho}} = \frac{\overline{P_d}}{\overline{P_d}} = \frac{\overline{P}}{\overline{P_d}}(1-\overline{x_v}) \quad (8')$$

gives $$\overline{w'\rho'_c} = \overline{\chi}\overline{w'\rho'_{cm}} + \chi_T\overline{w'T'\rho_{cm}} + \chi_{Pe}(1-x_v)\frac{\overline{P_{cm}}}{\overline{P_d}}\overline{w'\rho'_v}\alpha_v\overline{P} \quad (9')$$

where, $w'\rho'_c$ is raw flux in mol m$^{-2}$ S$^{-1}$ and $\overline{\rho_d}$ is number density of dry air (mol m$^{-3}$).

With a small change in notation, equation 24 of Webb et al. (1980) can be written as:

$$F_c = \overline{w'q_{c'}} + \mu\frac{\overline{q_c}}{\overline{q_d}}\overline{w'q_v'} + (1+\mu\sigma)\frac{\overline{q_c}}{\overline{T}}\overline{w'T'} \quad (10')$$

where $F_c$ is mass flux of a non-reactive gas (g m$^{-2}$s$^{-1}$) $q_i$m$\rho_i$ is mass density (g m$^{-3}$) of non-reactive gas (e.g. methane), dry air, or water vapor (subscripts c, d, or v) respectively, $\mu=m_d/m_v$=formula weight of dry air to molecular weight of water vapor, and $\sigma=\overline{q_v}/\overline{q_d}$.

Equation 9' can be rewritten in terms of mass flux by multiplying each term on both sides by the molecular weight of non-reactive gas (m$_c$) and the last term on the right by $m_d/m_v=\mu$ to give $$\overline{w'q'_c} = \overline{x}\overline{w'q'_{cm}} + \chi_T\overline{w'T'q_{cm}} + X_{Pe}\mu(1-x_v)\frac{\overline{q_{cm}}}{\overline{q_d}}\overline{w'q'_v}a_v\overline{P} \quad (11')$$

Substituting 11' into 10' and noting that $\overline{q'_c} = \overline{q_{cm}}X$:

$$F_c = \overline{X w' q'_{cm}} + X_T \overline{w' T' q_{cm}} + X_{Pe} \mu (1 - x_v) \frac{\overline{q_{cm}}}{\overline{q_d}} \overline{w' q'_v} a_v \overline{P} + \quad (12')$$

$$\overline{X} \mu \frac{\overline{q_{cm}}}{\overline{q_d}} \overline{w' q'_v} + \overline{X} (1 + -\mu \sigma) \frac{\overline{q_{cm}}}{\overline{T}} \overline{w' T'}$$

Rearranging and noting that $$1 + \mu \sigma = \quad (13')$$

$$\frac{1}{1 - \overline{x_v}} : F_c = \overline{X w' q'_{cm}} + \overline{X} \mu \frac{\overline{q_{cm}}}{\overline{q_d}} \overline{w' q'_v} + a_v (1 - \overline{x_v}) \overline{P} X_{Pe} \mu \frac{\overline{q_{cm}}}{\overline{q_d}} \overline{w' q_v} +$$

$$\overline{X}(1 + \mu \sigma) \frac{\overline{q_{cm}}}{\overline{T}} \overline{w' T'} + (1 - \overline{x_v}) \overline{T} X_T (1 + -\mu \sigma) \frac{\overline{q_{cm}}}{\overline{T}} \overline{w' T'}$$

Grouping like terms gives:

$$F_c = \overline{X} \left\{ \overline{w' q'_{cm}} + \mu \frac{\overline{q_{cm}}}{\overline{q_d}} \overline{w' q'_v} \left[ 1 + a_v (1 - \overline{x_v}) \overline{P} \frac{X_{Pe}}{X} \right] \right. \quad (14')$$

$$\left. (1 + -\mu \sigma) \frac{\overline{q_{cm}}}{\overline{T}} \overline{w' T'} \left[ 1 + (1 - \overline{x_v}) \overline{T} \frac{X_T}{X} \right] \right\}$$

where $$\left[ 1 + a_v (1 - \overline{x_v}) \overline{P} \frac{X_{Pe}}{X} \right]$$

is the latent heat multiplier and $$\left[ 1 + (1 - \overline{x_v}) \overline{T} \frac{XT}{X} \right]$$

is the sensible heat multiplier.

Equation 14' is a general form of propagation of T-P effects of a single-line or narrow range laser measurement into the Eddy Covariance flux measurements. Equation 14' assumes covariances of higher order terms in equations 4', 6' and 7' with wind speed can be neglected. If such is found not to be the case, equation 14' can be generalized accordingly.

Validation of the Proposed Method Using Specific Example of LI-7700 Methane Analyzer and Field Data The LI-7700 has a measurement response that is dependent on temperature and pressure. This T-P dependence comes from a number of effects: changes in the Boltzmann population distribution of the rotational levels, Doppler and pressure broadening of individual lines. All of these effects have been calculated for the following conditions: 50 to 110 kPa and from −40 to 50° C. These calculated absorption profiles were then run through the modulation/demodulation algorithm and the predicted responses were collected into a table. Table 1 is an example of those values for 90-100 kPa and 10-30 C range. A high-resolution look-up table would provide a more accurate value of $\chi$ for every specific time and set of conditions.

TABLE 1

Values of $\overline{X}$

| Pressure, kPa | 10 | 15 | 20 | 25 | 30 |
|---|---|---|---|---|---|
| 90 | 0.883 | 0.889 | 0.894 | 0.900 | 0.906 |
| 92 | 0.901 | 0.906 | 0.912 | 0.917 | 0.923 |
| 94 | 0.919 | 0.924 | 0.929 | 0.935 | 0.941 |
| 96 | 0.937 | 0.942 | 0.947 | 0.953 | 0.959 |
| 98 | 0.955 | 0.960 | 0.965 | 0.971 | 0.977 |
| 100 | 0.974 | 0.979 | 0.984 | 0.989 | 0.995 |

TABLE 2

Values of $\alpha_w \overline{P} \frac{X_{Pe}}{X}$.

Notice that to get the full water vapor multiplier, one must multiply this value by (1-$X_w$) and add unity.

| | 10 | 15 | 20 | 25 | 30 |
|---|---|---|---|---|---|
| 90 | 0.409 | 0.404 | 0.399 | 0.395 | 0.390 |
| 92 | 0.417 | 0.412 | 0.407 | 0.403 | 0.398 |
| 94 | 0.425 | 0.420 | 0.416 | 0.411 | 0.406 |
| 96 | 0.434 | 0.429 | 0.424 | 0.419 | 0.414 |
| 98 | 0.442 | 0.437 | 0.432 | 0.427 | 0.422 |
| 100 | 0.450 | 0.445 | 0.440 | 0.435 | 0.430 |

TABLE 3

Values of $\overline{T} \frac{X_T}{X}$.

Notice that to get the full sensible heat term multiplier, one must multiply this value by (1-$X_w$) and add unity.

| | 10 | 15 | 20 | 25 | 30 |
|---|---|---|---|---|---|
| 90 | 0.337 | 0.358 | 0.378 | 0.398 | 0.419 |
| 92 | 0.324 | 0.344 | 0.365 | 0.386 | 0.406 |
| 94 | 0.311 | 0.331 | 0.352 | 0.373 | 0.393 |
| 96 | 0.297 | 0.319 | 0.340 | 0.360 | 0.381 |
| 98 | 0.284 | 0.306 | 0.327 | 0.348 | 0.368 |
| 100 | 0.272 | 0.293 | 0.314 | 0.335 | 0.356 |

According to one embodiment, a method that accounts for broadening due to water vapor proceeds as follows:

I. Measure absorptance as a function of temperature and pressure over a range of methane concentrations, or use HITRAN, to establish a temperature and pressure response surface describing T-P effects. The function $\chi$ from Equation 1 is described as a result. Measure gas analyzer response in the presence of water vapor, or use literature values if available, to establish a water vapor broadening coefficient. The phrase T-P effects is understood to include effects of water vapor when such are needed.

II. Using a fast temperature or sensible heat flux measurement device near the gas analyzer; record fast temperature or sensible heat flux alongside fast measurements of gas density.

In the case when water factor in T-P effects is not negligible, a fast air water content or latent heat flux measurement device is used to record fast air water content or latent heat flux alongside measurements of fast gas density.

For the case of Eddy Covariance gas flux measurements, an anemometer device near the gas analyzer is used to record vertical wind speed alongside fast gas density.

III. Compute, measure, or estimate conventional sensible heat flux by any available method. In the case when water factor in T-P effects is not negligible, compute, measure, or estimate conventional latent heat flux by any available method.

IV. For the case of Eddy Covariance gas flux measurements, combine and align recorded time series of vertical wind speed and gas density on longer-term basis (minutes to hours), and compute raw uncorrected gas flux.

V. Use Equation 8' or 11' for unspecified or for empirically defined function $\chi$, or use equation 26 when $\chi$ can be defined by equation 16, for computing gas flux corrected for T-P effects on spectral absorption. Frequency of data collection (fractions of seconds to seconds) and averaging period (minutes to hours) are determined by the specific approach and purpose of the gas measurements.

Embodiments of the present invention make it possible to obtain gas flux corrected for T-P effects without the need for taking measurements of fast gas temperature or air water content integrated over the gas sampling volume. This enables the use of low-power open-path gas analyzers, and the use of reduced-power closed-path analyzers with short intake tubes. No such analyzers relying on a single line, or narrow absorption range, are currently available.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A gas analysis data handling device comprising:
   a processor;
   a communication interface to receive data from one or more measuring devices; and
   a memory store for storing data received by the communication interface, the processor configured to:
   receive a plurality data, the plurality of data including:
     a plurality of gas density measurement data for a target gas;
     a plurality of wind speed measurement data indicative of speed of movement of the target gas;
     a plurality of water vapor density measurement data indicative of water content in the target gas;
     a plurality of temperature measurement data; and
     a barometric pressure;
   determine a raw flux of the target gas based on the plurality of gas density data for the target gas and the plurality of wind speed measurement data;
   determine a water dilution effect based on the plurality of water vapor density measurement data;
   determine a thermal expansion value based on the plurality of temperature measurement data;
   determine an equivalent pressure based on the barometric pressure, the plurality of temperature measurement data, the plurality of water vapor density measurement data, and a water vapor broadening coefficient; and
   compute the gas flux of the target gas based on the raw flux, the water dilution effect, and the thermal expansion value, wherein at least one of the raw flux, the water dilution effect, or the thermal expansion value is adjusted by a multiplication factor determined based on an instrument response function of the instrument used to obtain the gas density measurement data, the response function relating actual gas density and measured gas density of the target gas as a function of temperature and equivalent pressure.

2. The device of claim 1, wherein each of the raw flux, the water dilution effect, and the thermal expansion value is adjusted by a respective multiplication factor determined based on an instrument response function of the instrument used to obtain the gas density measurement data, the response function relating actual gas density and measured gas density of the target gas as a function of temperature and equivalent pressure.

3. The device of claim 1 further comprising a non-transitory computer-readable memory connected to the processor, the non-transitory computer-readable memory having stored therein program code, the program code comprising:
   computer instructions configured to cause the processor to receive the plurality data;
   computer instructions configured to cause the processor to determine the raw flux of the target gas based on the plurality of gas density measurement data for the target gas and the plurality of wind speed measurement data;
   computer instructions configured to cause the processor to determine the water dilution effect based on the plurality of water vapor density measurement data;
   computer instructions configured to cause the processor to determine the thermal expansion value based on the plurality of temperature measurement data;
   computer instructions configured to cause the processor to determine the equivalent pressure based on an average barometric pressure, the plurality of temperature measurement data, the plurality of water vapor density data, and the water vapor broadening coefficient; and
   computer instructions configured to cause the processor to compute the gas flux of the target gas based on the raw flux, the water dilution effect, and the thermal expansion value, wherein at least one of the raw flux, the water dilution effect, or the thermal expansion value is adjusted by the multiplication factor.

4. The device of claim 1 wherein the response function includes calibration data of the instrument determined for an operating pressure substantially equal to the pressure at which the gas density measurement data was obtained.

5. The device of claim 1 wherein the barometric pressure is an average barometric pressure.

6. A gas analyzer system comprising:
   a gas analyzer having an optical path and operable to produce a plurality of gas density measurements when a target gas flows across the optical path;
   a pressure sensor configured to measure barometric pressure;
   a wind speed detector disposed in proximity to the gas analyzer;
   a temperature sensor disposed in proximity to the gas analyzer and clear of the optical path of the gas analyzer; and
   a controller configured to:
   receive a plurality of gas density measurement data obtained by the gas analyzer;
   receive a plurality of wind speed measurement data obtained by the wind speed detector;
   receive a plurality of temperature measurement data obtained by the temperature sensor;
   receive a plurality of water vapor density measurement data indicative of water content in the target gas;
   receive a barometric pressure;
   determine a raw flux term of the target gas based on the plurality of gas density measurement data and the plurality of wind speed measurement data;

determine a thermal expansion term based on the plurality of temperature measurement data;

determine an equivalent pressure based on the barometric pressure, the plurality of temperature measurement data, the plurality of water vapor density measurement data, and a water vapor broadening coefficient; and compute the gas flux of the target gas based on the raw flux term and the thermal expansion term, wherein at least one term being adjusted by a multiplication factor determined based on an instrument response function corresponding to the instrument used to obtain the gas density measurement data, the instrument response function relating actual gas density and measured gas density of the target gas as a function of temperature and equivalent pressure.

7. The system of claim 6, wherein the barometric pressure is an average barometric pressure.

* * * * *